(12) United States Patent
Zhang et al.

(10) Patent No.: US 7,636,988 B2
(45) Date of Patent: Dec. 29, 2009

(54) METHODS FOR MAKING FASTENERS

(75) Inventors: Zhiqun Zhang, Roseville, MN (US); Janet A. Venne, Roseville, MN (US); Dennis L. Becker, Vadnais Heights, MN (US); Lori-Ann S. Prioleau, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 11/530,499

(22) Filed: Sep. 11, 2006

(65) Prior Publication Data

US 2008/0060173 A1 Mar. 13, 2008

(51) Int. Cl.
*A44B 18/00* (2006.01)
(52) U.S. Cl. .............................. 24/442; 24/306; 24/451
(58) Field of Classification Search .................. 24/306, 24/442–452; 428/143; 264/167
See application file for complete search history.

(56) References Cited

U.S. PATENT DOCUMENTS

| | | | |
|---|---|---|---|
| 2,370,636 A | 3/1945 | Carlton |
| 2,447,374 A | 8/1948 | Smyser |
| 3,550,837 A | 12/1970 | Erb |
| 3,922,455 A | 11/1975 | Brumlik |
| 4,615,084 A | 10/1986 | Erb |
| 5,092,910 A | 3/1992 | DeKok |
| 5,230,851 A | 7/1993 | Thomas |
| 5,315,740 A | 5/1994 | Provost |
| 5,380,390 A | 1/1995 | Tselesin |
| 5,496,386 A | 3/1996 | Broberg |
| 5,540,673 A | 7/1996 | Thomas |
| 5,549,962 A | 8/1996 | Holmes |
| 5,679,302 A | 10/1997 | Miller |
| 5,879,604 A | 3/1999 | Melbye |
| 6,039,911 A | 3/2000 | Miller |
| 6,054,091 A | 4/2000 | Miller |
| 6,248,276 B1 | 6/2001 | Parellada |
| 6,287,665 B1 | 9/2001 | Hammer |

(Continued)

FOREIGN PATENT DOCUMENTS

WO   WO 01/33989   5/2001

(Continued)

OTHER PUBLICATIONS

U.S. Appl. No. 60/825,220 filed Sep. 11, 2006.

*Primary Examiner*—Robert J Sandy
(74) *Attorney, Agent, or Firm*—Aleksander Medved

(57) ABSTRACT

There is provided a hook fastener comprising a base, where at least one surface has a multiplicity of engaging projections, which projections have a top surface and an attached end that are arranged in a region to form one or more shapes. There is also provided a method for forming the above fastener comprising dispersing onto a contact release surface polymer particles in at least one discrete area forming a predetermined shape and forming preform projections. The front surface of the base is fixed to the terminal ends of at least some of the preform projections and then removed from the contact release surface in the form of the predetermined shape. In an alternative method polymer particles are uniformly dispersed onto a contact release surface using electrostatic attraction and selectively transferred to the base in the predetermined shape by masks or selective adhesion or the like.

22 Claims, 14 Drawing Sheets

U.S. PATENT DOCUMENTS

| | | | |
|---|---|---|---|
| 6,470,540 B2 | 10/2002 | Aamodt | |
| 6,569,494 B1 | 5/2003 | Chambers | |
| 6,588,073 B1 * | 7/2003 | Zoromski et al. | 24/446 |
| 6,592,800 B1 | 7/2003 | Levitt | |
| 6,627,133 B1 | 9/2003 | Tuma | |
| 6,669,745 B2 | 12/2003 | Prichard | |
| 6,678,924 B2 * | 1/2004 | Murasaki et al. | 24/452 |
| 6,692,674 B1 | 2/2004 | Kurtz, Jr. | |
| 6,708,378 B2 | 3/2004 | Parellada | |
| 6,730,069 B2 * | 5/2004 | Tanzer et al. | 24/442 |
| 6,752,700 B2 | 6/2004 | Duescher | |
| 6,962,635 B2 | 11/2005 | Tuman | |
| 7,044,989 B2 | 5/2006 | Welygan | |
| 2001/0018110 A1 * | 8/2001 | Tuman et al. | 428/99 |
| 2003/0038408 A1 | 2/2003 | Schulte | |
| 2003/0104746 A1 * | 6/2003 | Menzies et al. | 442/328 |
| 2004/0031130 A1 | 2/2004 | Clarner | |
| 2004/0172792 A1 * | 9/2004 | Kurtz, Jr. | 24/442 |
| 2005/0241119 A1 * | 11/2005 | Efremova et al. | 24/442 |

FOREIGN PATENT DOCUMENTS

WO    WO 2006/099000    9/2006

\* cited by examiner

ALL REFERENCES CONSIDERED EXCEPT WHERE LINED THROUGH. /RS/

ALL REFERENCES CONSIDERED EXCEPT WHERE LINED THROUGH. /RS/

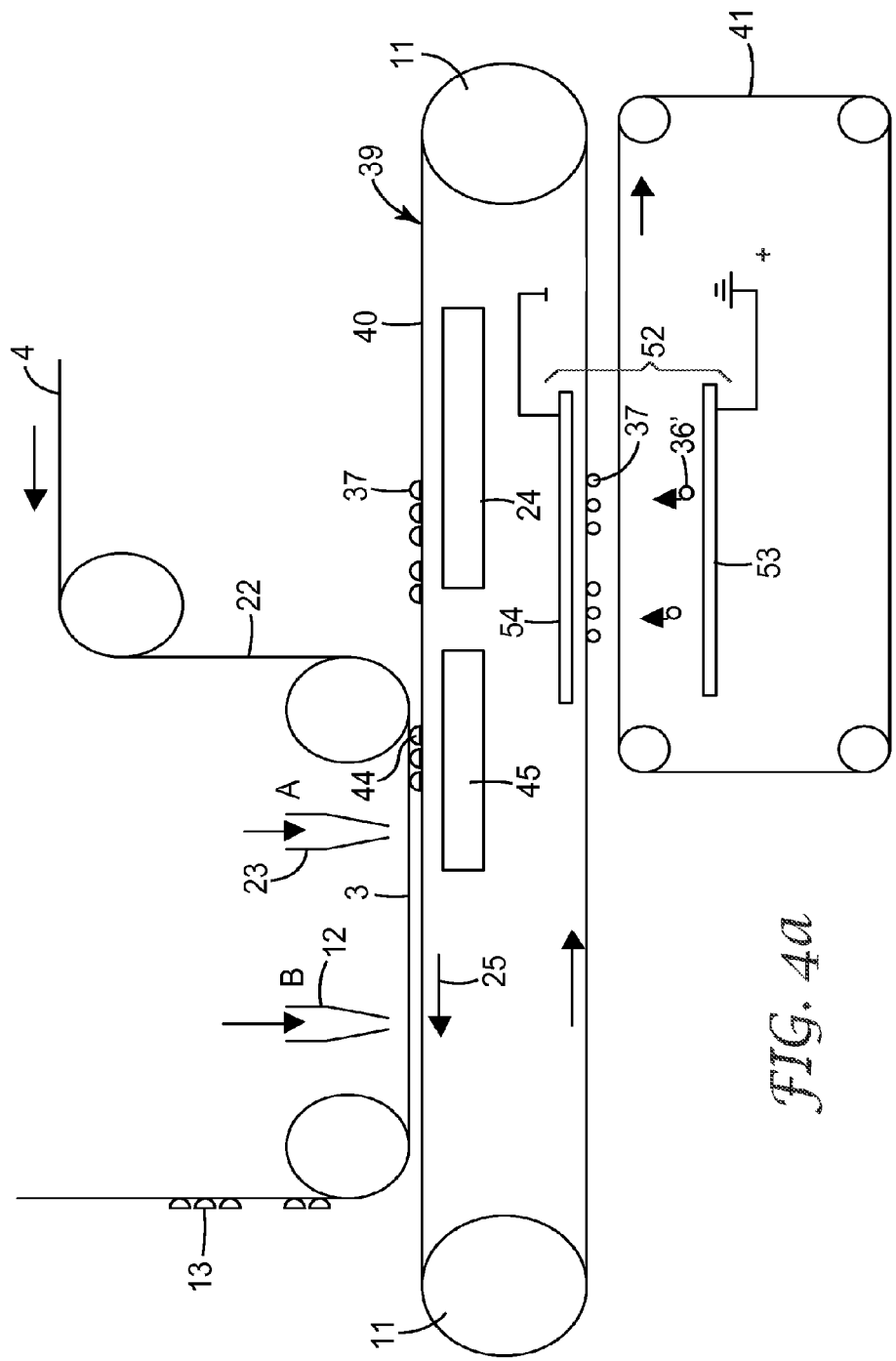

ALL REFERENCES CONSIDERED EXCEPT WHERE LINED THROUGH. /RS/

ALL REFERENCES CONSIDERED EXCEPT WHERE LINED THROUGH. /RS/

Downweb

ALL REFERENCES CONSIDERED EXCEPT WHERE LINED THROUGH. /RS/

US 7,636,988 B2

METHODS FOR MAKING FASTENERS

TECHNICAL FIELD

The present invention relates to methods of manufacturing fasteners, particularly male components for fasteners of the touch-and-close type, also known as hook-and-loop type fasteners.

BACKGROUND OF THE INVENTION

It is common to use certain types of hook-and-loop type mechanical fasteners for fixing disposable diapers, training pants and incontinence garments around a wearer. One approach is a thin, molded male fastener with low loft loop materials, preferably nonwoven, fabrics as the female components. For these uses generally low cost, soft touch, appropriate strength and increasing stretch in the waistline are important.

Hooks can be directly molded as disclosed for example in U.S. Pat. No. 5,315,740, assigned to Velcro, which discloses molded hooks with low displacement volumes so that it needs only to displace a small volume of loop fabric in order to engage therewith. The patent discloses a re-entrant hook, i.e., whose tip-portion curves over and down toward the base sheet from the upper end of the hook to define a fiber-retaining recess on the underside of the hook.

It is also known to cap molded stems on webs. Mushroom-shaped engaging projections obtained by this process are disclosed in U.S. Pat. No. 5,679,302 and U.S. Pat. No. 5,879,604 in which an extruded polymer layer is pressed against a mold with mold cavities, the cavities producing projecting stems, integral with the base. The terminal ends of the stems are then deformed with a heated pressure roller, forming the loop engaging projections. U.S. Pat. No. 6,054,091 discloses a similar method in which, however, the heated deforming surface gives an essentially lateral deformation to the stems during the deformation thereby forming re-entrant, J-shaped hooks with flat top portions. The solution of U.S. Pat. No. 6,627,133 differs from the previous ones in that the stemmed web, to be capped with a heated pressure roller, is manufactured with the method of U.S. Pat. No. 6,287,665, i.e., with a special mold constituted by a cylindrical printing screen. All documents mentioned in this paragraph are similar in that they flatten preformed stems by a hot roll.

US Patent Application 2004/0031130A1 discloses a method in which a product, comprising a polymer base and stems integral with and projecting from a base is extrusion-molded with a mold roll having a multiplicity of sophisticated mold cavities. The distal ends of the stems are then heated and melted while their feet are kept cold and solid. The melted ends are then flattened with a deforming surface. The same approach, i.e., pre-heating and successively flattening stems, appears in U.S. Pat. No. 6,592,800, U.S. Pat. No. 6,248,276 and U.S. Pat. No. 6,708,378, the latter ones also disclosing capping with a rough contact surface, creating roughened flat tops of engaging projections.

U.S. Pat. No. 6,039,911 discloses a stem-deforming apparatus comprising a long variable nip, e.g., a pair of co-operating conveyors, which gradually compressively deform the stems, unitary with the base.

U.S. Pat. No. 6,470,540 uses a hot extruded layer for deforming stems, which results in semi-spherical mushroom heads.

In U.S. Pat. No. 3,550,837 a male fastener member is described whose each engaging projection is constituted by an irregularly shaped granule with a special multifaceted surface, adhesively adhered to the base. The fastener is suitable for securing a flap of a disposable carton against opening. Engaging is provided by the granules comprising a number of tiny flat planes forming a multifaceted surface.

In U.S. Pat. No. 3,922,455 nibs of various shapes are grafted onto linear filaments, the linear filaments, protruding from a base, forming the engaging elements of a male fastener component.

In PCT publication WO 01/33989, particles are, with a scatter head of a scatter coater, randomly scattered, and fixed, onto a base. Each engaging projection is constituted by several agglomerated particles, though some individual particles may also be left present.

It was therefore an object of the present invention to provide low-cost male mechanical fasteners with advantageous properties. It was another object of the present invention to provide commercially attractive alternatives to the mechanical male fastener systems available so far and methods for making them.

BRIEF DESCRIPTION OF THE INVENTION

The present invention provides a hook fastener capable of engaging a suitable loop fabric comprising a base with a front surface and a back surface, where at least one surface has a multiplicity of engaging projections having a top surface and an attached end. The attached end is fixed to the surface of the base where a plurality of said projections are arranged in a region to form one or more shapes.

In a preferred method polymer particles are dispersed onto a contact release surface using electrostatic attraction to impact the particles onto the contact release surface.

In more detail the present invention provides a fastener for engaging with a loop fabric comprising a base with a front surface and a back surface, where at least one surface has a multiplicity of engaging projections having a top surface and an attached end, which attached end is fused to the surface of the base where a plurality of said projections are arranged to form one or more shapes. (Thereafter herein, the engaging projections are referred to as being attached to the "front" surface of the base. This is done for purposes of illustration and encompasses attachment of engaging projections to either surface). The engaging projections are arranged in a nonuniform distribution in a region so as to collectively form one or more predetermined shapes on the base. These shapes are preferably discrete and can create functional hook regions adjacent nonfunctional or lower functional hook containing regions. The shapes can be determined by functional or artistic considerations and can extend continuously along a dimension of the base or be discrete islands within a front or back surface of the base. Preferably the at least some engaging projections top surface ends form an edge angle surrounding the projections, with a mantle surface extending from the top surface edge to the attached end; at least one contour line of a side view of the mantle surface being strictly convex from a top surface edge to the attached end.

The present invention furthermore provides a fastener, as described above, for engaging with a loop fabric, comprising a base having a front surface with a multiplicity of engaging projections at least some of the engaging projections having a top surface end and an attached end. The engaging projections attached ends are fixed or preferably fused to the front surface of the base and the top surface forming an edge at least partially surrounding the projection.

The present invention also provides a first subset method for forming a fastener comprising:

providing a multiplicity of suitable polymer particles;
providing a base with a front surface;
dispersing onto a contact release surface a multiplicity of polymers particles in at least one discrete area of the contact release surface forming a predetermined shape;
providing the polymer particles, dispersed on the contact release surface, in a semiliquid state of a suitable viscosity, at least some of the particles in the discrete regions or areas being in contact with the contact release surface for a time sufficient to transform into preform projections;
conducting and fixing the front surface of the base with the terminal ends of at least some of the preform projections;
removing the base from the contact release surface thereby separating the preform projections fixed thereto,
thereby forming engaging projections projecting from the front surface of the base in the form of a predetermined shape.

The polymer particles are generally dispersed into a predetermined shape as preform projections by use of a masking surface where particles impact the masking surface and those particles passing though the masking surface forming the predetermine shapes. The polymer particles can be impacted onto the masking surface by gravity, electrostatic attraction, impaction or other suitable forces or any combination thereof. The preform projections on the contact release surface are then transferred to the base, retaining approximately the same predetermined shape, so as to form engaging projections approximately of the predetermined shape.

In a preferred method polymer particles are dispersed onto a contact release surface using electrostatic attraction to impact the particles onto the contact release surface.

The present invention also provides a second subset method for forming a fastener comprising:
providing a multiplicity of suitable polymer particles;
providing a base with a front surface;
dispersing onto a contact release surface a multiplicity of polymers particles;
providing the polymer particles, dispersed on the contact release surface, in a semiliquid state of a suitable viscosity, at least some of the particles in discrete regions or areas being in contact with the contact release surface for a time sufficient to transform into preform projections;
conducting and fixing the front surface of the base with the terminal ends of at least some of the preform projections in a predetermined region or area of the base;
removing the base from the contact release surface thereby separating the preform projections fixed thereto, thereby forming engaging projections projecting from the front surface of the base in the form of a predetermined shape.

The polymer particles can be selectively adhered in these predetermined regions or areas by providing for preferential adhesion to the base in these predetermined areas. Preferential adhesion could be accomplished by providing areas with adhesion promoting layers or treatments, or providing areas with adhesion deterring layers or treatments, including a removable mask. It is also possible to combine the two methods; that is by depositing the particles onto the contact release surface in a predetermined area, thereafter transferring the particles onto the base in a predetermined area with preferential adhesion to the particles.

The present invention also encompasses the use of adhesives in various methods and configurations. Such adhesives can include any of the wide variety of adhesives (hot melt, UV cure, etc.) that are known in the art, but preferably include pressure sensitive adhesives, as described herein and referred to hereafter by the term PSAs. A PSA can be provided on the base front surface for example in discrete areas adjacent the predetermined regions of engaging projections described above or on the base back surface or both.

The male mechanical fasteners of the invention can also be used in disposable diapers. In a preferred embodiment the fastener is capable of engaging with the nonwoven outer shell of a diaper strongly enough to securely keep the soiled diaper in a folded state. Further, preferably the engagement with the nonwoven outer shell of a diaper is strong enough to secure the diaper around a wearer during use, thereby making a separate frontal tape, of a special loop fabric, in the landing zone unnecessary, which can provide considerable cost saving.

The male mechanical fasteners of the present invention can also be used to form a so-called back-to-back wrapping tape that has the fastener of the present invention on one face thereof thereby offering such new possibilities, deriving from the invention, such as an inexpensive, highly flexible still strong, very thin or easily cut wrapping tape. In a preferred embodiment, the wrapping tape can be easily written upon with a pen. In another preferred embodiment the wrapping tape may be elastically stretchable and can be advantageously used for packaging or technical (e.g. cable wrap) applications.

BRIEF DESCRIPTION OF THE DRAWINGS

FIG. 1b is a segmented top view of a masking surface used in the apparatus of FIG. 1a.

FIG. 1c is an enlarged cross sectional view of the fastener of FIG. 1a.

FIG. 2b is a segmented top view of a masking surface used in the apparatus of FIG. 2a.

FIG. 3b is a segmented top view of a first masking surface used in the apparatus of FIG. 3a.

FIG. 3c is a segmented top view of a second masking surface used in the apparatus of FIG. 3a.

FIG. 4a is a schematic side view of a fourth apparatus for manufacturing a fastener of the invention.

FIG. 4b is a segmented top view of a masking surface used in the apparatus of FIG. 4a.

FIG. 5b is segmented top view of a patterned electrode belt used in the apparatus of FIG. 5a.

FIG. 6b is a segmented top view of a base film with regions of preferential adhesion used in the apparatus of FIG. 6a.

FIG. 7b is a segmented top view of a masking surface used in the apparatus of FIG. 7a.

DETAILED DESCRIPTION OF THE INVENTION

Figure 1A:
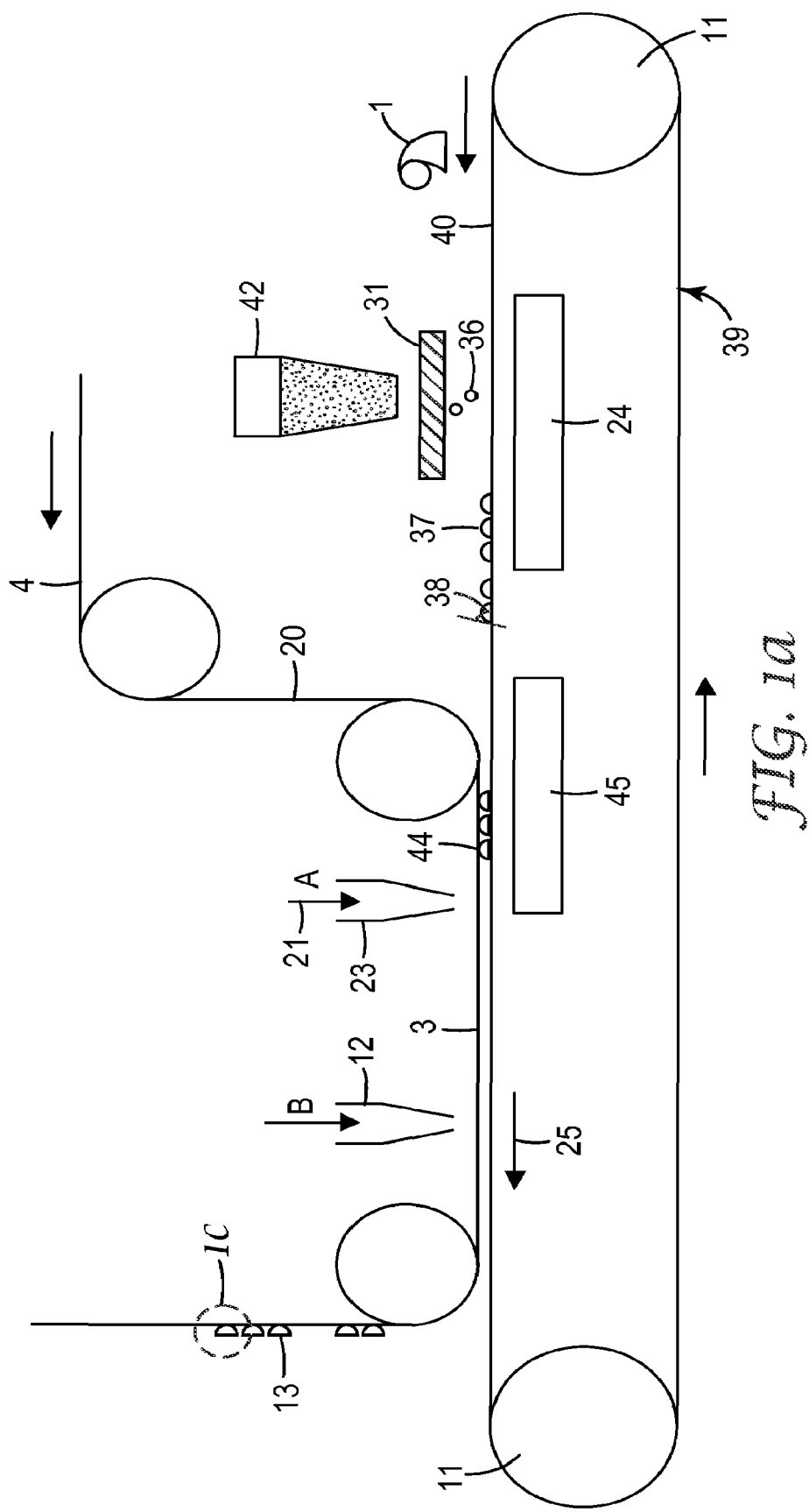
FIG. 1a is a schematic side view of the apparatus for manufacturing a fastener of the invention.

The present invention provides a fastener for engaging with a loop fabric. The fastener comprises a base having a front surface with a multiplicity of engaging projections arranged into predetermined patterns or shapes formed by a multitude of the engaging projections. Namely a plurality of engaging projections together create a shape on a base based on their size and/or density being different than in adjacent areas of the base, the shape is one that is generally clearly visible to the naked eye. As shown in FIG. 1c, at least some of the engaging projections 13 have a top surface end 14, where at least some engaging projections top surface ends 14 form an edge angle 18 surrounding the projections 13. Opposite the top surface end 14 is an attached end 16, which is attached to the front surface 20 of the base 4. There can be a mantle surface 17 extending from the top surface 14 edge 15 to the attached end 16. The mantle surface 17 in some embodiments has at least one contour line of a side view of the mantle surface 17 that is strictly convex from a top surface edge 15 to the attached end 16, as shown in FIG. 1c.

The present invention furthermore provides a fastener for engaging with a loop fabric, comprising a base 4 having a front surface 20 with a multiplicity of engaging projections 13 arranged in to predetermined patterns or shapes at least some of the engaging projections having a top surface end 14 and an attached end 16, which attached end 16 is fixed or fused to the front surface 20 of the base 4 and the top surface 14 forming an edge 15 at least partially surrounding the projection 13.

Figure 8C:
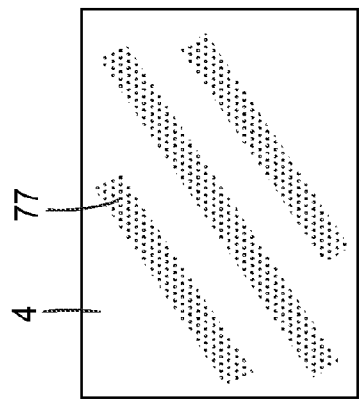
FIGS. 8a-8d are segmented top views of alternative shapes possible using methods of the invention.
Figure 8B:
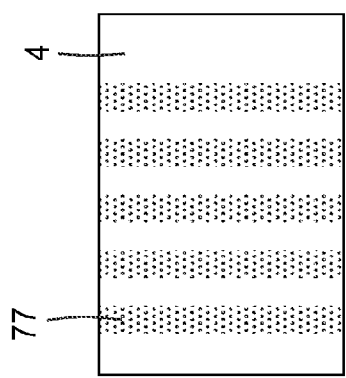
Figure 8A:
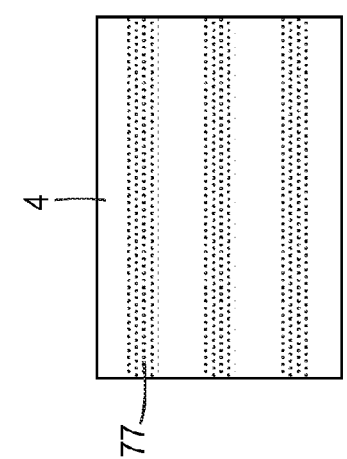

The hook fastener can have plurality of engaging projections form a discrete or continuous shape. Shape is defined as a plurality of the engaging projections that are organized into a specific area or region, where there are more or less, or different types or sizes, of engaging projections outside this region. A shape does not need to have defined edges but rather could have a gradual change in the density or distribution of the engaging projections from, e.g., a high density engaging projection area to an adjacent low density engaging projection area. This low density engaging projection area could have little or no hook engaging projections. Preferably the shape is formed by the plurality of engaging projections in a region having a relatively high density of engaging projections. The plurality of engaging projections forming a shape can extend substantially continuously in one dimension of the base as shown in FIG. 8a. The shapes in most embodiments will have a minimum width dimension less than the width of the base as it should not cover the entire surface of the base The shapes could be surrounded by secondary areas having a either a different type and/or density of engaging projections. In a preferred embodiment the shapes are relatively high density regions having an average density of engaging projection of at least 1 gram per square meter (gsm) of particles, or at least 2 gsm of particles which are of a general average size of about 50 to 1000 microns or generally 50 to 500 microns. (Note that the engaging projection average size, and density of the engaging projection material, can be used to convert this measurement to the number of engaging projections per area). In another alternative the secondary regions have an average density of engaging projections of less than about 50 percent of the average density of engaging projections in the shape region, or less than about 25 percent of the average density of engaging projections in the shape region. In a preferred embodiment at least one region will have little or no engaging projections. For those shapes that extend continuously in one dimension of the base the shapes generally will have a minimum width dimension less than the width of the base. The shapes generally would have a minimum width dimension of greater than 1 mm or greater than 4 mm.

The shaped regions of engaging projections may be provided on a base layer that is a continuous web. The regions of engaging projections can be present as a plurality of regions on the surface of the continuous web, for example in a repeating or nonrepeating pattern of regions bearing engaging projections, partially or completely surrounded by regions lacking any engaging projections (or, as discussed herein, bearing engaging projections that are present at a lower density, or that differ in some property such as size, height, color, aspect ratio, etc.). Various potential shapes that engaging projection regions 77 may form on a base film 4 are illustrated in FIGS. 8a-8d. The shaped regions bearing engaging projections may be present as discrete regions within a contiguous area that has no engaging projections (or, that have differing engaging projections as discussed above); or, the engaging projections may be present in a contiguous area that has regions of no (or fewer, or different) engaging projections interspersed therein.

The engaging projection regions or areas can serve a wide variety of functions. The basic premise is that of providing one or more sets of engaging projections only in the regions in which they are desired to be present on the substrate (base). Such regions of engaging projections may provide benefits in terms of adhesion, cost, ornamental or visual effect, or some other factor. A example is the placement of a hook containing region (strip, rectangle, or shape as desired) on an article in a predetermined desired location. This is customarily done by making a uniform hook material on a backing, such as a film, and cutting discrete pieces of this hook material and bonding it to the article where fastening functionality is desired (for example onto a sheet of material that is to be used as a diaper side panel, ear, or backsheet). This is typically done by use of adhesives or melt bonding. The current method allows regions of engaging projections to be formed directly on the desired article in the size and location desired. For example, engaging projections may be placed in desired regions on a continuous web, intended to be used as a diaper side panel, ear or backsheet, etc. from which individual pieces bearing the engaging projections may then be taken (for example by die-cutting), to form a diaper side panel, ear or backsheet, etc.

It is also possible to provide the regions of engaging projections so as to impart unique or novel mechanical performance. For example, the engaging projections can be present in the form of regions (for example, strips), separated by regions without engaging projections, or with a lower density (that is, the number of engaging projections per unit area of the base film), of engaging projections, or with larger or smaller engaging projections, etc. Such configurations may provide enhanced or tailored properties, for example in peel or shear behavior. For example, regions of low shear or peel properties can be interposed with regions of high shear or peel properties, which might serve to provide more uniform performance when a fastener is disengaged from a loop substrate. Or, a region with a lower density of engaging projections (which, again, includes regions of no engaging projections) may serve as a fingerlift zone, for example in use as a diaper closure. If engaging projections are applied in regions in a multistep process the regions can overlap in whole or in part which can result in a certain number of "stacked" projections resulting from the deposition of preform projections onto existing preform projections. The presence and amount of stacked projections can also be tailored to achieve desired engagement properties.

Figure 9A:
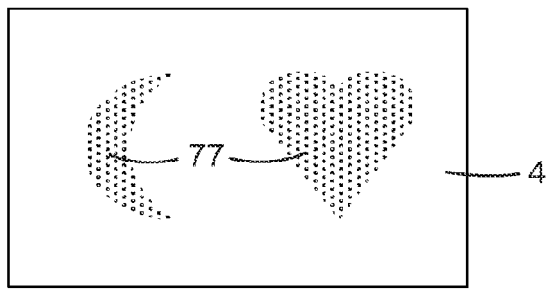
FIGS. 9a and 9b are segmented top views of alternative design shapes possible using methods of the invention.

The engaging projection regions can also be provided so as to impart novel and unique visual or ornamental effects. The engaging projections can be provided in a region that is shaped so as to form a recognizable image or shape, e.g. an object, a letter, or the like, as exemplified in FIG. 9a. Multiple shapes could be provided to create a more complex image or shape or be repeated in simple patterns. These visual effects can be augmented by providing the engaging projections in one or more colors (via use of pigmented materials, etc.), or by the use of reflective additives, and so on.

Figure 9B:
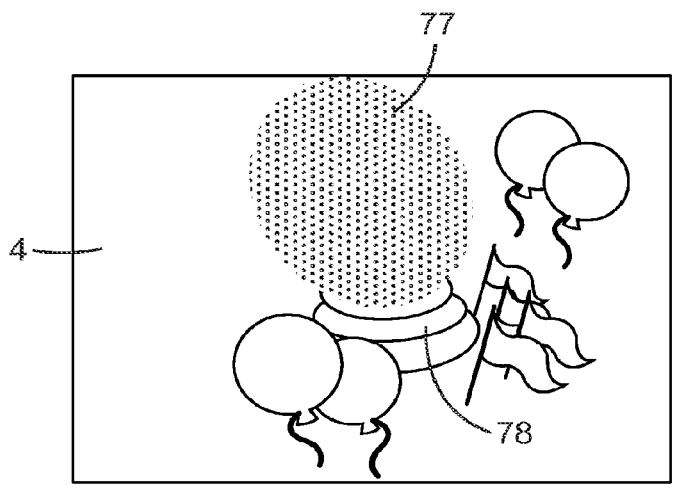

One alternative embodiment of providing unique visual or ornamental effects is to provide the engaging projections on a base that has preprinted graphic elements. (The preprinted graphic elements can be present on the top surface or bottom surface of the base layer, depending on whether or not the base layer is transparent.). The region of engaging projections could be used as a graphic element in conjunction with the preprinted graphic elements. For example, the base layer can be preprinted with a visual image or scene (e.g. a garden), and the region of the engaging projections can then be deposited in the shape of a flower. The shaped engaging element region may be placed at random in the preprinted visual image. Or the shaped engaging element region may be placed into a predetermined location in the preprinted visual image, as shown for example in FIG. 9b, in which a shaped engaging projection region 77 is placed in a preprinted visual image 78 on a base film 4. The engaging projections can also be provided so as to comprise a background in a predetermined region (for example, the engaging projections could appear to be individual snowflakes in a landscape scene).

The engaging projections are provided by means of depositing preform projections onto a surface of a preprinted base. The preform projections may be deposited in areas, which are not imaged (i.e. do not bear ink, pigment, metalized coating, etc). Alternatively the preform projections can be deposited onto imaged areas as long as the imaging layer is such that the preform projection can be bonded satisfactorily to it. Or, if the imaging layer is sufficiently thin, it may be possible to fuse the preform projection to the underlying base front surface, through the imaging layer, by deforming, melting, or otherwise displacing the imaging layer.

As mentioned, the polymer particles used to form the engaging projections can be colored, tinted, pigmented, etc., for specific visual purposes. Multiple regions can be provided with different color engaging projections, or different densities or sizes of engaging projections, for specific visual effects.

The present invention also encompasses the use of adhesives, preferably pressure sensitive adhesives (PSAs). Such PSAs include a wide variety of materials known in the art, for example, natural rubber adhesives, block copolymer-based PSA's (for example, those based on elastomers available from Kraton Polymers, of Houston Tex.), acrylate-based PSA's, and silicone-based PSA's. PSA's may be chosen so as to bond well to polyolefinic thermoplastic materials (e.g. polypropylene, polyethylene, and copolymers and blends of the same), and might include, for example, the family of PSAs available from 3M Company under the designation LSE (e.g., LSE 300). Other suitable compositions may be based on silicone-polyurea based pressure sensitive adhesives. Such compositions are described in U.S. Pat. No. 5,461,134 and U.S. Pat. No. 6,007,914, for example.

Figure 10:
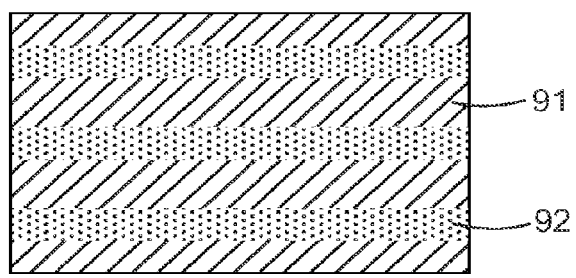
FIG. 10 is a segmented top view of a fastener possible using methods of the invention having adhesive areas adjacent hook containing regions.

In one embodiment, the PSA may be provided in an area adjacent the region bearing engaging projections. Either or both the PSA and engaging projection regions may be present as discrete or continuous regions. For example, in FIG. 10 is pictured downweb stripes 91 of PSA adjacent to downweb stripes 92 of engaging projections.

The base used in the methods of the invention can be any suitable continuous or discontinuous base web such as a porous or nonporous polymer film, a laminate film, a nonwoven web, a paper web, a metal films and foils or the like. The base could be modified by any known method such as by being printed, embossed, flame treated, laminated, particle coated, colored, or the like. A polymer film used as a base can be oriented or unoriented. In conjunction with the methods described later, the base film can be provided such that it possesses areas that vary in the ability to bond to the preform projection, which is yet another way of providing a substrate with engaging projection regions present in discrete shapes, patterns, and the like. The base film surface can be smooth, or can be provided with features such as projections or valleys molded into the base which could be used as ripstops, tear propagation lines or other features, which could be on the front or rear face of the base.

The surface of the base can also be roughened, for example with particles previously scattered and fixed thereon. The particles should be brought and fixed on the base 4 in a way that at least the terminal ends of the projections can be formed from the particles. Projections can consist completely of the particles without any further modification of said particles. For bringing and fixing the particles to the (smooth or roughened) front surface, several methods are taught, e.g., random scattering and adhering, for example, in the cited PCT publication WO 01133989, the entire disclosure of which is hereby incorporated by reference.

The word "particle", as used herein, refers to a solid, liquid or semi-liquid particle, including, for example, granules, pellets, powders and droplets. Appropriate particles can be selected based on the discussions herein. If the embodiment of this invention relying on electrostatic deposition of particles (as described later herein) is used, the particles should be chosen so as to be compatible with this process. In electrostatic deposition, particles are moved under the influence of an electric field so as to impinge on the base (whether onto selected regions or uniformly onto all regions of the base). Thus, in this instance the particles must be susceptible to having an electric charge imparted to them (otherwise they would not move under the influence of the electric field). Such methods are well known in the art and the selection of such particles is straightforward.

In terms of the properties of the engaging projections that are formed from the particles, it is preferable if at least some engaging projections are provided with a side view which strictly tapers from the top surface or top surface edge to the attached end at the front surface of the base. As used herein, a side view means a view taken perpendicular to the front surface of the base. Strictly tapering means that the nearer the engaging projection gets to the base, the narrower the projection becomes. For example, a cylinder is not a strictly tapering shape. This type of tapering will pull engaged fibers down to the front surface of the base when a shear load is applied to the fastener without the fibers being caught at a nontapered portion displaced from the front surface of the base. Thus the torque on the engaging projection is minimal so the base can be weaker, i.e., can be cheaper, more flexible, more skin friendly, thinner etc. Furthermore, the fastener may have a relatively large surface area formed by the projection tops, making the fastener smooth to the touch, while also having a relatively low total surface area of the projection attached ends connected to the base, increasing the flexibility and skin-friendliness of the fastener. The engaging projections can also be characterized by a ratio of the perimeter of area of the engaging top to the height of the engaging projection, which is generally 1.1 to 50, and is preferably 1.2 to 20. The engaging projection also generally forms an overhanging rim, which generally is the difference between the top surface area and the area of the attached end.

Turning from the materials used to the methods of the invention, a preferred general set of methods for manufacturing a male fastener component with predetermined shapes of engaging projections in accordance with the invention generally comprises the basic steps of:

providing a base with a front surface;

providing particles of polymer material;

providing a contact release surface of a suitable surface energy;

dispersing, on the contact release surface, a multiplicity of the polymer particles;

bringing or providing the polymer particles into an at least semi-liquid or softened state of a suitable viscosity, providing preform projections (preform projection signifies a projection that to at least some extent has been preformed into the shape of the final engaging projection) sitting on and projecting from the release surface. The preform projections along their edges contacting the contact release surface will form contact angles, which contact angle is influenced by the surface energies of the polymer particles and the contact release surface. The polymer particles are maintained in a semiliquid state for a suitable period of time so that they form an acute contact angle;

the preform projections can then be at least partially solidified for contacting and fixing to the front surface of the base with the terminal ends of at least some of preform projections, while essentially maintaining the shape of the edge formed by the contact release surface;

the preform projections are then further solidified sufficient to separate and remove the preform projections from the contact release surface thereby forming engaging projections attached to the base. These formed engaging projections project from the front surface of the base to flattened tops, which tops were formed on the contact release surface. The flattened tops at least partially overhang the base forming a rim, and are bordered, at least partly, by an edge having an angle which is influenced by the acute contact angle.

Figure 8D:
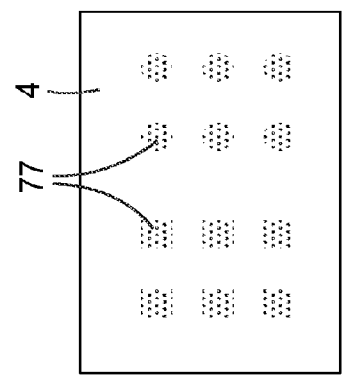

As mentioned above, there are two generic subsets of methods that allow the formation of predetermined shapes of engaging projections. In the first subset method the polymer particles are deposited onto the contact release surface in a predetermined pattern that defines the shape to be formed. The particles are delivered to the contact release surface in selected patterns or shapes by a variety of methods. In a first method the particles are projected against a mask having cutout portions that define the shape to be formed. The mask can be fixed in position, with the result that particles that go through the cutout portion of the mask are deposited as preform projections onto the (moving) contact release surface in stripes. An exemplary engaging projection area configuration resulting from this approach (upon transfer of the preform projections to a base film) is shown in FIG. 8a. The deposition of particles can be stopped and started so as to provide interrupted downweb stripes. Alternatively, the mask can move with and at about the same speed as the contact release surface. In this case, the particles that go through the cutout portion of the mask are deposited on the contact release surface in the shape defined by the cutout. Some exemplary engaging projection area configurations resulting from this approach are shown in FIGS. 8b, 8c and 8d. The mask can comprise a disposable film, for example a plastic film with appropriately shaped cutouts. In a preferable embodiment, the mask comprises an endless belt (as discussed later with regard to the embodiment of FIG. 2a).

The particles are projected onto or through the mask by any of a variety of means. First, gravity could be used where particles are simply allowed to fall onto the mask. This method however suffers from the problem of how to remove the particles that land on the non-cut out portions of the mask. These particles could be removed by vacuum, contact removal, air jets or the like, but there remains the possibility that some of these particles later fall through the apertures of the mask in areas not intended to have particles, or at the wrong time in regions intended to have particles.

Another way to bring particles onto or through a mask is electrostatic deposition. In this method the polymer particles are directed toward the mask by an electrostatic driving force. This is performed by providing two electrodes so as to establish an electric field therebetween. A first electrode is positioned so that the mask is between the first electrode and the contact release surface. A second electrode is positioned behind the contact release surface. A voltage is applied to the electrodes so as to establish an electric field therebetween. Upon the introduction of suitable particles into the gap between the first electrode and the mask, the particles are changed then driven under the influence of the electric field in the direction of the second electrode. Thus, the particles encounter the mask, with the result that some hit the solid portion of the mask and some pass through the cutout regions and impinge on the contact release surface so as to collectively form the desired shape.

Electrostatic deposition is most advantageously performed in a vertical configuration with the second electrode positioned above the first electrode. In this arrangement the particles are driven upwards, against gravity, thus the particles that hit the mask fall back down and may be collected and/or recycled, or are otherwise less likely to accidentally fall onto the contact release surface, which is present behind the mask and the contact release surface. This method also has the advantage of providing for more uniform distribution of particles onto the contact release surface. All the particles will be like charged and repel one another. This will tend to keep the particles evenly distributed and keep individual particles from forming large number of unified preform projections. This method is advantageous for providing either uniform distributions of particles in the discrete regions or over the contact release surface as a whole with a uniform distribution of particles to be formed into preform projections.

As previously described herein, the mask may be stationary or moving in tandem with the contact release surface. (An embodiment of the latter is discussed in detail later with regard to the embodiment of FIG. 2a). In electrostatic coating, ideally the mask material is such that the particles that hit the mask do not stick to it via electrostatic attraction.

The polymer particles must also be chosen for their suitability for electrostatic coating. The primary requirement is that under the influence of the imposed electric field, the particle develop sufficient induced charge such that sufficient force is placed on the particle by the electric field that the particle moves between the two electrodes. Preferably, the electric force should overcome gravity such that the above-described vertical configuration can be used. Fortunately, most of the materials that are appropriate for forming preform projections (namely, thermoplastic powders such as polypropylene and the like) are dielectric materials (that is, capable of having a charge induced upon being placed in an electric field). Suitable particles for forming the preform projections are also generally small and of low density (thus light in weight) making them easier to be driven via electrostatic force upward against the force of gravity.

An alternative embodiment of electrostatic discrete deposition uses a second electrode that is in the form of a patterned conductive belt. Such a patterned belt, placed behind the contact release surface (above the release surface, if in the vertical configuration), moving in tandem with the release surface, would result in particles being moved toward the contact release surface primarily in the regions of the release surface that have a solid area of the patterned electrode behind them. This eliminates the need for a physical mask interposed between the particle source and the contact release surface. Such a patterned belt most conveniently takes the form of a continuous metal belt with holes provided therein, which can be connected to a voltage source and maintained at a desired voltage even while moving in an endless loop. (Such an embodiment is discussed in more detail with regard to the embodiment of FIG. 5a) This arrangement is most suited for deposition of preform projections in a contiguous pattern with discrete empty areas therebetween. If it is desired to provide the preform projections in discrete regions surrounded by contiguous empty areas, it is possible to use a nonconductive belt with conductive regions provided thereon (for example, a nonconductive polymeric film with areas of conductive ink screen printed thereon). It would of course be necessary to provide electrical connection between the conductive areas, which could be done with very thin lines of conductive material. As described previously, the particles are introduced into the space between the first electrode and the mask (if present). Alternatively, in the absence of a mask, the particles are introduced into the space between the first electrode and the contact release surface. The particles should be placed in the gap in whatever manner will allow them to come under the influence of the electric field and be driven toward the contact release surface. Ideally, this is performed in a uniform manner. The particles may be sprayed, dropped, blown, or otherwise injected into the gap by methods well known in the art. In the above-described vertical configuration, the particles may be injected laterally into the gap by spraying. Alternatively, the particles can be brought into the gap by means of a carrier belt which, bearing the particles on its top surface, comes into the gap such that the particles are free to move toward the contact release surface by the applied electric field.

Other methods besides the afore-mentioned electrostatic deposition and gravity-assisted deposition are possible. Alternative methods to selectively bringing particles to a contact release surface in predetermined shapes or patterns include impacting the particles onto a mask by a forced airstream, mechanical projection or conveying, and the like.

These first generic subset methods are amenable to multi-step deposition of particles as preform projections. That is, it may be advantageous to provide different discrete regions that comprise engaging projections that differ in some feature (for example, color, size, aspect ratio, modulus, etc.). One such way to provide such a product is to process a base film to attach one set of engaging projections, then send the film through an additional processing step to attach a second set. However, this may involve cumbersome handling of the base film. A preferred method is to provide a processing line with multiple deposition stations. That is, it is possible to deposit a given set of preform projections onto the contact release surface, and thereafter deposit another set of preform projections. The second set may be deposited in (separate) discrete regions, or may be deposited throughout the contact release surface (which will of course result in some degree of "stacked") projections. Such a configuration may be provided by means of a processing line that has two deposition stations positioned sequentially such that the moving contact release surface passes through one station, then through the other station. After passing through the deposition stations, the preform projections are transferred to the (same) base film. (An example of this is discussed in additional detail with reference to the embodiment of FIG. 3a). In an alternate configuration, the first set of preform projections may be deposited on the contact release surface then transferred to the base film, which is then fed into the second deposition station for deposition and subsequent attachment of the second set of preform projections.

In a second generic subset of methods the polymer particles are deposited onto the contact release surface, which could be uniformly. The predetermined pattern or shape of engaging projections is provided by selectively transferring and attaching polymer particles on the contact release surface onto predetermined regions of the base. This selective attachment can be done by making predetermined regions of the base more or less receptive to bonding the preform projection polymers. Two basic approaches exist. The first is to provide a base film that has little or no ability to bond to the polymer particles used to form the preform projections, and then imparting regions of higher bonding ability onto the surface of the base film. In the use of an adhesive such as a PSA to bond the preform projections to the base, it would be straightforward to provide the PSA on the base only in selected regions (by pattern coating, stripe coating, and the like). In the case of fusing (i.e. melt bonding), dissimilar polymeric materials may not bond well to each other. Thus, for example, the placement of preform projections of polystyrene onto a base film of polypropylene, (or vice versa) may result in little or no bond formation. However, if a compatibilizing layer is placed upon a selected area of the polypropylene base film, an enhanced bond may be achieved. Such compatibilizing layers can be applied to the base in a patterned or discrete or discontinuous manner by a wide variety of methods of the art, including pattern coating, screen printing, vapor coating, plasma coating, photolithography, chemical vapor deposition, and the like.

Compatibilizing layers may comprise any of the widely known tie layers and bonding layers that are available in the art. All that is necessary is that the compatibilizing tie layer have sufficient adhesion to the base and sufficient adhesion to the polymer particle used to form the preform projection. In this approach, the polymer particles and base film may no longer need to be formed of the exact same material, or materials that are extremely close or similar in composition. This allows the base and the polymer particles to be chosen based on the physical properties most desired for each. For example, it may be desirable to chose a base film that is extremely soft and flexible, and a polymer particle that is extremely hard and rigid (or vice versa). The use of compatibilizing layers on the base film allows this to be done. An example of this approach is discussed later with regard to the embodiment of FIG. 6a.

The other approach is to use a base and polymer particles that bond well to each other, and to apply a masking layer to selected regions of the base. In one embodiment the masking layer is a permanent layer that is retained on the base and that does not bond to the polymer particles. Such masking layers could be polymeric (for example, coatings such as silicone, fluorosilicone, or Paralene) or metal or metal oxides, for example. All that is necessary is that the layer does not bond well to the particles nor is it sufficiently displaceable to permit bonding to occur through it. Such layers can be applied to the base in a patterned or discrete or discontinuous manner by a wide variety of methods of the art, including pattern coating, screen printing, vapor coating, plasma coating, photolithography, chemical vapor deposition, and the like. It is also possible to deposit the masking layer everywhere on the surface and to remove it in selected regions, via etching, ablating, and the like.

In another embodiment the masking layer is provided temporarily, so as to constitute a physical barrier in certain locations to prevent polymer particles from contacting the base during transfer from the release surface. In this case the masking layer may be a film which is used temporarily but does not become part of the final product, as described later with reference to the embodiment of FIG. 7a.

The skilled person, familiar with the field of surface energy, surface tension and wetting, can select a combination of a suitable polymer for the particles and a contact release surface of a suitable surface energy, and also select particles having a suitable viscosity at the temperature of the contact release surface that will wet the contact release surface within a suitable time. The surface energy of the contact release surface may be formed by known materials and methods, such as siliconized surfaces, fluorochemicals, corona discharge, flame or the like. The contact release surface must be able to release the particular polymer particles used, semi-liquefied and solidified. It is known that certain release surfaces can release certain polymers but are unable to release other polymers. For example, a polyethylene release surface can release suitable polypropylene particles but cannot release certain polyethylene particles as they tend to weld or fuse to each other. The word "release" as used herein refers to the phenomenon where the particles are detached from the contact release surface without (unacceptable) damage or loss of material of the particles or preform projections.

Dispersing of the particles onto the contact release surface by gravity can be performed in any suitable way, for example, by scattering the particles with a scatter unit. Other methods have been mentioned herein. The particles should be dispersed at a rate per unit surface area so that they form preform projections where one particle can form one preform projection, which may merge as discussed above. The particles can be brought into the at least semi-liquid state before, during and/or after dispersing of the particles onto the contact release surface. "At least semi-liquid" means liquid or semi-liquid. A suitable way of liquefying will depend on the properties of the selected polymer, and can include, for example, heating, thinning, solving, emulsifying, dispersing etc.

A solidity (degree or extent of solidification) suitable for contacting and fixing the preform projections on the contact release surface with the front surface of the base can be decided by the skilled person, depending on the particular circumstances. It will usually, but not necessarily, mean a more solid state than the one in which the preform projections have been formed on the contact release surface. Preferably the preform projections should be solid enough to keep, at least partly, their shape while being contacted with the front surface of the base. It usually primarily means keeping at least a minimum free height and also a suitable edge angle of the preform projections. Setting the necessary solidity in the preform projections will be material-dependent, and can include cooling, drying, heating, crosslinking, curing, chemical treatment etc. The preform projections of suitable solidity, sitting on the contact release surface, can be covered by the base front surface such that the front surface of the base can contact and fix with the preform projection terminal ends. The terminal ends are the ends farthest from the contact release surface. Before contacting with the front surface of the base, the preform projections can be provided, or supplemented, with further added dispersed particles or the like, which will attach to the preform projections. It is possible that the front surface of the base is contacted with the preform projections when the preform projections are in a semiliquid state. In this case it is possible that after the contacting, and before a final solidification, the preform projections are somewhat lengthened by stretching while the preform projections are removed from the release surface thereby causing the preform projections to get slimmer in their middles. A skilled person can also choose a base flexible enough to permit contacting preform projections of possibly non-uniform heights. The front surface of the base can be smooth but it can also be suitably rough, for example roughened with particles or projections previously scattered and fixed on the base. The fixing of the terminal ends of the preform projections to the front surface of the base can be obtained for example by, adhering with an added adhesive (for example, a pressure sensitive adhesive, hot melt adhesive, or UV-cure adhesive), crosslinking with ultraviolet irradiation, or it can utilize the inherent adhesion of the contacting materials (the base front surface or the preform projections) or fusing. Fixing with fusing will be discussed in detail later herein. While fixing, care should be taken in order that the free overhangs or rims, and the actual heights of the preform projections are sufficiently preserved. For example, an exaggerated sinking or compression of the projections into the front surface of the base should be avoided. The proper solidity of the preform projections and the base, suitable for a separating and removing both from the release surface can be decided by the skilled person, depending on the particular circumstances. The solidity of the preform projections when they are removed from the release surface will usually, but not necessarily, be a more solid state than when they are initially contacted with the front surface of the base. Preferably the preform projections should be solid enough to keep, at least partly, their shape during the separation from the release surface. It usually primarily means keeping a suitable overall shape, with particular respect to the edge angle formed, but preserving a suitably strong bond with the front surface of the base is also an important factor. The base generally should be solid enough to keep its form and separate the preform projections from the release surface. The flattened top surface as formed can be smooth but can also be somewhat roughened, e.g., sandpaper-like or grooved, as known from the art. The top surface structure will be largely determined by the contact release surface, which may be essentially flat, even if naturally not planar in the true geometrical sense. Post treatments could however be used that would make the top surface not essentially flat, such as a noncontact heat treatment. If small numerous projections are advantageous it is preferable if, in the methods, that at least some of the separate preform projections comprise exactly one polymer particle per preform projection.

It is preferable if, in the methods, at least some of the preform projections are provided with contact angles 38 of between 10° and 85°, preferably 30° and 80°. This would be the range of contact angles for most of the individual preform projections. For a preferred embodiment this range would be the mean contact angle for the preform projections.

It is preferable if, in the methods, at least some engaging projections are provided with a profile in which, in each side view thereof, the engaging projection strictly tapers (preferably is strictly convex) from the flattened top or top edge to the front surface of the base. This is usually very easy to achieve by this method which typically creates semi-lenticular preform projections, like water drops sitting on a suitable surface. In the methods, non-thermoplastic and thermoplastic polymer particles can be used, the selection being based on necessary strength, required surface energy, cost etc. However it is preferable if, in the methods the polymer particles are thermoplastic polymers.

If drops of liquids are deposited onto a solid contact release surface and if the surface energy of the release surface is somewhat higher than the surface energy (or surface tension) of the liquid, the liquid will typically perfectly wet the solid, with a contact angle of zero. With liquids, each "solid-liquid" pair has a contact angle, between zero and 180°, with which the liquid drop will, approximately, wet the solid. With semi-liquid, e.g., softened thermoplastic, particles, the process of forming a contact angle is a time-temperature phenomenon. With solid contact release surfaces of high surface energy a liquid polymer will wet perfectly if given enough time. If this high surface energy solid contact release surface is kept hot, and a cold solid particle is placed thereon, a process is started in which the contact angle transforms over time, from an initial obtuse angle towards the final zero contact angle. By interrupting this transformation process, e.g., by a suitable cooling, one can achieve any desired contact angle. Therefore high surface energy solid contact release surfaces are useful in the process of the invention. However, the higher the contact release surface's surface energy, the more difficult it is to finally separate the release surface from the preform projections. Also if the surface energy of the contact release surface is too high in relation to that of the polymer particles there is greater opportunity for unintentional operator error forming a preform projection that excessively wets the contact release surface. The danger of overwetting the contact release surface is lower if the surface energy of the contact release surface is not higher than the surface energy of the particle plus 60 mj/m².

High surface energy contact release surfaces also might cause the engaging projection's edge angles being too sharp creating rims that are too thin and which might possibly break off during later use, creating undesired contamination. It is likely sometimes better to accept larger contact or edge angles to provide enhanced security against engaging projections forming with thin weak edges and rims. Therefore it can be preferable if the methods comprise providing a contact release surface whose surface energy is lower than the first surface energy (that of the particle). In this case the edge angle in the product can be determined by material selection rather than by on-line operating parameters. Also the lower the surface energy of the contact release surface, the easier it is to finally detach the preform projections therefrom. However a certain degree of force needed for detaching preform projections from the contact release surface can be beneficial. Some preform projections can be weakly fixed to the front surface of the base. Namely the fixing strength is lower than desired for its intended end use resulting in some engaging projections possibly breaking loose during use. This is a difficult to detect defect. Therefore it is preferable if the contact release surface's surface energy is higher than the first surface energy (that of the particle) minus 23 mJ/m². With a contact release surface of this level the separation force for detaching preform projections from the contact release surface may be high enough to remove projections weakly fixed to the base front surface thereby providing an on-line fault-detection and correction mechanism.

It is preferable if, in the methods described hereinabove for thermoplastic preform projections (which can also be termed protrusions throughout), the fixing of the front surface of the base with the terminal ends of at least some of the preform projections comprises fixing by heat or fusing.

Fixing by heat can include melting one or the other of the preform projections or the base front surface, depending on the materials and pressure etc. Preferably both the preform projections and the front surface of the base are allowed to potentially melt, and are thereby fused. Fusing is a fixing of the preform projections to the front surface of the base by heat. In this case the preform projections are made up of particles well suited for both sharpening by the release surface, from below, and the covering and fixing to the base by fusing, above. The particles must be liquefied enough during the fusing to suitably form the contact angle, but must remain solid enough, to permit keeping their edge angles. It is preferred that the thermoplastic polymer particles have a melt flow rate of between 1 and 90 grams per 10 minutes at the conditions appropriate for the selected polymer.

In the subsequent step of the above method, the fixing by heat comprises maintaining the contact release surface at a temperature lower than the softening temperature of the polymer particles or preform projections while contacting the front surface of the base with the attachment ends of at least some of the preform projections. The back surface of the base is preferably heated by subjecting it to a heated gas. However, other heating methods such as radiant or IR heat may be used. If heated gas is used, the gas pressure at the back surface of the heated base is typically higher than the pressure (e.g. a gas pressure) at the front surface of the heated base, thereby pressing the heated base against the attachment ends of at least some of the preform projections to enhance the fixing thereof to the base. The pressure difference may be enhanced, for example, by applying vacuum from beneath the contact release surface or the front surface of the base.

Also, in these methods it is not a great problem if the preform projections are of different heights, as long as a sufficiently pliable base, capable of bending down to reach the lower preform projections, is provided. It is especially useful if the whole base is thermoplastic and is actually softened, thereby made soft and flexible, easily bending or even stretching when hot (This may be advantageous particularly if regions of preform projections differing in height are present, as discussed previously). If desired the base can be fully softened, where fully softening means softening of all components, layers thereof, e.g. in case of a composite, above a softening temperature.

After the separation of the base from the release surface, some preform projections, not fixed to the base, may remain on the contact release surface. These are usually very tiny residual polymer particles, which may melt into, and go away with, particles dispersed later on the contact release surface. Still by regularly providing for their removal from the contact release surface, the process can be made more uniform and secure. Therefore it is preferable if the method further comprises:

before the dispersing of the multiplicity of polymer particles on the contact release surface;

heating the contact release surface to a temperature higher than the softening temperature of both the polymer particles and the front surface of the base;

contacting the front surface of the base with the heated contact release surface thereby softening the front surface;

suitably pressing the softened front surface against the heated contact release surface thereby fusing the polymer particle contamination residue into the front surface of the base;

providing, for the contact release surface and the base, temperatures suitable for separating the base from the contact release surface;

separating the base from the release surface, thereby cleaning the contact release surface.

This method uses the thermoplastic character of both the particles and the front surface of the base for cleaning the contact release surface. During the steps above, the small amount of residual polymer contamination goes away with, and usually disappears in the front surface of the base. The base can then be utilized as usual. In a continuous operation, e.g. comprising rolls or conveyors, the release surface can be cleaned with every revolution, before each dispersing of particles, thus always keeping the cumulative contact release surface contamination at low levels.

While the preform projections are being fused to the front surface of the base, the base is typically above the release surface where it is supported by the preform projections and bridges the space between them. If the front surface of the base is above its softening temperature, any molecular orientation therein may cause problems by shrinking at least the bridging portions of the sheet-form base. That can be avoided, for example, with using a composite base with a suitable backing resistant to shrinking. For example a base, comprising a polyester film, or paper, backing and a polyethylene layer coated thereon as front surface, can potentially withstand the shrinking that may occur in the base. However if shrinkage is a problem it is preferable if the base is free of molecular orientation when fusing the preform projections or particles. Molecularly oriented films can be pretreated by contacting the front surface of the base with a heated release surface (which could be the contact release surface), thereby rendering the front surface of the base essentially molecularly un-oriented.

Heated gas (preferably air) at an elevated pressure can best be provided with gas nozzles ejecting heated gas. If the base is moved in front of the output orifice of the nozzles so that its back surface is contacted with the ejected hot gas then the base softens. At the same time, the hot gas ejected from the nozzles creates and maintains a gas flow along the back surface of the base, typically parallel to the traveling direction of the base. If the nozzles are fixed and the base is moving in a machine direction, the hot gas flow will have a direction essentially both parallel and opposite to the machine direction. The hot gas flow, e.g. hot air flow, will exert a pulling force on the softened base, dragging the back surface of the base. That will tend to stretch the softened base. The faster the gas flows, the stronger this stretching effect will be. With a low throughput arrangement, i.e., with low hot gas velocities, and especially with a thick base, a base which is essentially free of molecular orientation can be used. In case of higher throughputs and higher gas flow rates, and especially with a thinner base this machine direction stretching of the base can be very significant, which can be undesirable. For example, stretching of the base in a lengthwise, machine direction can make it difficult to control the thickness of the fastener or can result in rolls of unspecified length. Stretching can also lead to accidental breaking by thinning, tearing apart the base.

The effects of stretching can be counterbalanced by providing a suitable molecular orientation in the base. The problem of stretching can be solved if the base is provided with a heat-shrink potential in the machine direction. The heat of the gas will relax the orientation in the base, i.e., will tend to shrink the base, which will counteract stretching by the heated gas flow. Therefore, in a variation of the invention method, one or more gas nozzles, adapted for ejecting heated gas, are provided. The back surface of the base is contacted with the heated gas ejected by the one or more gas nozzles while the base moves relative to the one or more gas nozzles. The direction in which the base is moving is the machine direction and is essentially within the plane of the base. The base preferably has a heat-shrinkability in the machine direction (the lengthwise heat shrinkability) of at least 1 percent. The fixing by heat includes heating the base above a heat shrink temperature thereof.

As used herein, "heat-shrinkability" in a direction shall mean, in the context of a material such as the base material, that the material is capable of being decreased in its length in the given direction, or dimension, in response to the transmission of thermal energy into the material. The "heat shrinkability" of the material is a percent value and equals 100 percent times the difference between its pre-shrink length and post-shrink length, divided by its preshrink length, in the given direction. The post-shrink length, in a given direction, of the material means the length of the material, in the given direction, after shrinking the material, such as at a temperature of 170° C. for 45 seconds. Shrinking can be determined, for example, by immersing the material into hot silicon oil and letting it freely shrink. It was found that using temperature of 140° C. for 14 seconds relaxes essentially all the shrink in usual polymer materials. As used herein, the "shrinking temperature" of a material refers to the temperature at which the material, exposed to an increasing temperature, starts to heat-shrink.

The advantage of this variation of the methods of the invention is that it helps counteract stretching effects exerted on a softened base by ejected hot gas flow. With high production rates lengthwise heat-shrinkability higher than 1 percent can provide improved results. Therefore it is preferable if, in this variation of the methods, a base having a lengthwise heat-shrinkability of at least 10 percent, more preferably at least 20 percent, more preferably at least 30 percent, even more preferably at least 40 percent, and even more preferably at least 50 percent is provided for the contacting and the fixing depending on the forces created by the hot gas flow and the production rate.

The stretching effect, exerted on the base by a lateral hot gas flow is less significant, or even close to zero (depending on the details of the nozzle arrangement) in the crosswise direction, i.e., in the direction perpendicular to the direction of the traveling path of the base (in a machine it is called the cross machine direction). Therefore, if a base has a high heat-shrink potential, or high heat-shrinkability in the crosswise direction, the edges of the base can shrink or neck in, which results in folding or wrinkling when contacted with the hot gas. This is undesirable. Therefore it is preferable if the heat-shrinkability, of the base in its in-plane direction perpendicular to the main or machine direction is either zero, or lower than the lengthwise heat-shrinkability. "Zero crosswise heat-shrinkability", as used herein, includes the case in which the base exhibits an increase in length, or stretch, rather than shrinking, in the crosswise direction when exposed to heat. The advantage of this difference in heat shrinkability is that it provides a differentiated counteraction to the differentiated dragging effects of the hot gas flow on the softened base in the two orthogonal dimensions. Generally the heat-shrinkability, of the base in its in-plane direction perpendicular to the main direction (the crosswise direction) is lower than 50 percent. Preferably, the crosswise heat-shrinkability is lower than 40 percent, more preferably lower than 30 percent, even more preferably lower than 25 percent, depending on the forces created by the hot gas flow and the production rate. On the other hand, the base heated by the hot gas will exhibit a crosswise thermal expansion which may cause wrinkles in the product. That can be counterbalanced with a suitably low, but positive level of heat-shrinkability provided in the base in the crosswise direction. Therefore it is preferable, if, in the aforementioned situation, the crosswise heat-shrinkability of the base is at least 1 percent.

The methods of the invention also include the step of dispersing the polymer particles on the contact release surface so as to form separate preform projections. Preferably it should be avoided that many or most particles, which will form the preform projections, touch adjacent particles, or preform projections, before the preform projections are completed and solidified (However, such an instance may be preferable if it is desired to form "stacked" projections as described earlier). Premature particle contact results in a unifying of the neighboring particles or preform projections. However if in a fastener the engaging projections are close to each other, the fixing strength of the fastener is generally higher, i.e., the fastener performs better. As in this method the dispersing, e.g., scattering, of the particles is typically implemented as a stochastic process, the closeness of the projections usually does not reach the theoretically possible maximum value, i.e., the projections could even be a bit closer to each other in the end product. After the fastener is completed, a subsequent moderate heat shrinking of the base can improve the relative closeness of the fastener engaging projections if desired. However, in order to perform this step the base of the formed fastener must have some heat-shrinkability. Therefore it is advantageous if, in this variation of the methods of the invention, the formed fastener base, has a residual lengthwise heat-shrinkability of at least 1 percent. Preferably, a formed fastener base, has a lengthwise heat-shrinkability of at least 5 percent, more preferably at least 10 percent, more preferably at least 15 percent, even more preferably at least 20 percent, even more preferably at least 25 percent in this embodiment. In this method the formed fastener is subsequently heat-shrunk at least in the main direction. This heat-shrinking can be by any suitable way of transmission of thermal energy into the formed fastener but preferably in a way such that the acute contact angles, and the geometric features of the engaging projections in general, are kept essentially intact or are at least suitably protected. Preferably the heat energy is transmitted into the formed fastener from the back surface of the base of the fastener. For example this could be done by depositing hot material, e.g., hot melt adhesive, onto the back surface of the base as part of a fixing of the fastener to a substrate. The heat-shrinking should be kept at a low enough level so as to keep adjacent engaging projections separate from each other sufficient for the engaging fibers of a female fastener part to penetrate between adjacent engaging projections. Preferably the fastener base is heat-shrunk by about 0.1 to 25 percent or less.

Economical base materials, e.g., blown or cast thermoplastic polymer films, may not be readily or economically available with the appropriate heat shrink parameters, as these films often have higher heat-shrinkability values than are required. A suitable base can be produced from these economical base materials with a pre-treating step. The pre-treating suitably decreases the heat-shrinkability of the materially in a controlled, partial relaxing of its molecular orientation without letting it shrink entirely. Namely, if a high heat shrinkable film is mechanically kept from freely shrinking and is simultaneously kept hot or softened, its heat-shrinking potential or heat-shrinking capability will gradually decrease with time without the material actually decreasing in length or area to the corresponding extent. Therefore it is preferable if these types of base materials are pre-treated prior to contacting and fixing of the base material front surface with preform projections. The pre-treating of the base comprises providing a pre-treating release surface;

heating the pre-treating release surface to a suitable temperature higher than the softening temperature of the front surface of the base;

contacting and pressing the front surface of the base with the pre-treating release surface thereby softening the front surface;

keeping the softened front surface in contact with the heated pre-treating release surface while preventing the base from shrinking freely, for a suitable period of time thereby decreasing at least its lengthwise heat-shrinkability;

providing, in the pre-treating release surface and in the base, temperatures suitable for separating the base from the pre-treating release surface; and separating the base from the pre-treating release surface.

The release surface used for the pre-treating, i.e., the pre-treating release surface can be similar to or different from the contact release surface discussed above. The pre-treating release surface must be able to suitably release the base at the right time. The base preferably is essentially prevented from any shrinking, e.g. in order to maintain its regular dimensions, but mainly its length. This could be done by keeping the base front surface in full contact with the pre-treating release surface. For that purpose, the tack between the softened front surface of the base and the pre-treating release surface (e.g., a polytetrafluoroethylene surface) can be exploited. In order to do this residual air between the two surfaces should preferably be removed while contacting and pressing the base to the pre-treating release surface. The lengthwise heat-shrinkability of the base is decreased to a suitable value while the crosswise heat-shrinkability rate may (and preferably will) also be decreased. The longer the contact time and higher the temperature, the more the decrease in the heat-shrinkability will be, and vice-versa.

It may be desirable if the length of the base at the start of the process is not too much different from, or equivalent to, the length of the fastener product made therefrom, at the end of the process. As it was seen, this can be influenced by setting the right lengthwise heat-shrinkability in the pre-treated base. Therefore it is possible that in the pretreating process a decreased value of lengthwise heat-shrinkability is achieved such that the pre-treated base length is essentially the same as the formed fastener length. Within this method step if the balance decreased value can be continuously maintained by regulating, during the pre-treating of the base, one or both of;

the temperature of the pre-treating release surface, and the duration of the base contact with the pre-treating release surface.

A practicable manufacturing arrangement using a pre-treating step is using an endless release belt with a release outer belt surface kept in a circulating motion along a belt path; and for pre-treating the base a first portion of the outer belt surface, being at a first location of the belt path, is used as the pre-treating release surface; and for forming the fastener from the pre-treated base a second portion of the outer belt surface, being at a second location of the belt path suitably displaced from the first location, is used as the contact release surface; and the base is provided in the form of a continuous base film kept in a motion synchronous with the belt, and is contacted with the outer belt surface at the first and second locations.

This solution is advantageous because a single release belt is used for pre-treating the base and further producing the fastener from the pre-treated base, which can provide for a zero length-difference between the initial base and the final product. This zero length-difference is desired to conveniently use the same belt, running in all of its points with the same speed, for two different purposes, i.e., for pre-treating the base on the one hand and for depositing the particles to form preform projections and contacting and fixing the pretreated base therewith on the other hand. The release surface speed at the first location is desirably the same speed as the initial base speed and the release surface speed at the second location is desirably the same speed of the final formed fastener product. If the decreased value of lengthwise heat-shrinkability of the base provided by the pre-treating deviates from a balance value, this section of the base when in free contact with the belt between the first and second belt locations will tend to either get shorter or longer. That can be detected by providing a base film buffer with dancing roller(s) and detecting the trend of motion of the dancing roller(s). If the free section of the base film between the two belt locations should shorten then the lengthwise heat-shrinkability of the pre-treated base could be decreased and vice versa. The lengthwise heat-shrinkability of the pre-treated base can be decreased more by elevating the temperature of the belt at the first location and/or lengthening the first portion of the outer belt surface along which the belt and the base are in contact thereby lengthening the duration of the pre-treating of the base, and vice-versa. This solution has an additional advantage that the outer release belt surface is cleaned from any potential polymer particle contamination by contacting the softened thermoplastic front surface of the pre-treated base with the release belt with every revolution of the belt.

It is further the object of the present invention to provide a new fastener product, readily achievable through the methods above, having corresponding advantages.

The product of the invention is a hook fastener for engaging with a loop fabric, comprising a sheet-form base having a front surface with a multiplicity of solid and preferably essentially solid or rigid engaging projections. The engaging projections have a top end and an attached end (which can also be termed throughout as a foot). The attached end is joined to the base front surface at a fixing portion. In that there is a fixing of the engaging projections to the front surface of the base, the base and the engaging projection can be formed of different materials or the same materials. The engaging projections projecting from the base front surface can be formed to have an essentially flat top by the contact release surface. However, generally the top end has been subject to a deformation treatment such that it has a different form than the attached end of the engaging projection. If the deformation surface and/or the contact release surface are flat then the top end will be correspondingly flat as formed. The top will also generally overhang the base at least partly, where the overhanging portion is also referred to as a rim.

The top of the engaging projection as formed will also have a definite edge bordering the top. The engaging projection will also have a mantle surface, meeting the top along the edge, extending from the edge of the top to the attached end of the engaging projection at the front surface of the base. The mantle surface and the top surface close to form acute edge angles generally along the entire edge.

During use, the engaging projections should essentially behave as solid bodies fixed to a base, which preferably is flexible. As used herein, a strictly convex contour line of an engaging projection, in a side view is convex when looking from the outside and not straight. A strictly convex shape for the lower surface of the overhanging rim or mantle surface has been found to be beneficial because it gives a relatively large thickness to the at least one engaging projection. In at least one side view of the at least one engaging projection, the mantle surface is preferably strictly convex at least at a part thereof adjacent to the edge. This convex shape provides strength to the edge of the rim overhanging the base. A convex shape also effectively leads engaging fibers down towards the base, thereby reducing torque load on the engaging projections and the base where they are attached, as was discussed above. In a different preferred embodiment the engaging projection is strictly tapered from the top to the front surface of the base in at least one side view of the at least one engaging projection.

The invention fastener has desired advantages. It can provide good shear strength engagement with low loft loop fabrics, including ultra thin nonwoven fabrics. It can also provide shear strength in all directions and is therefore essentially isotropic. The invention fastener can also be manufactured with dense and small projections with generally flat tops and a flexible base making it skin-friendly. There is great flexibility in selecting the base relative to the particles forming the engaging projections. The invention fastener can also be low cost.

Preferred forms of the product, some of them corresponding to the preferable embodiments of the methods described above, can offer various advantages.

First it is advantageous if the fastener engaging projections, in at least one side view of the mantle surface are strictly convex at least in all portions adjacent to the side edge. Further, it is advantageous, if the fastener engaging projections in each side view of the mantle surface are is strictly convex at least in all portions adjacent to the side edge. It is also advantageous if the fastener engaging projections, in each side view strictly tapers from the top to the front surface of the base. The mantle surface 17 and the top surface 14 of the engaging projections define edge angles 18. These edge angles 18 are advantageously along the entirety of the edge and have an angle of between 15° to 85° or between 30° and 80°. It is further advantageous if the fastener at least one engaging projections 13, are strictly convex in at least one side view of the entire mantle surface 17. This effectively leads the engaging fibers down to the front surface 20 of the base 4, to reduce torque load. It is further advantageous if the fastener comprises engaging projections 13, which are strictly convex in each side view of the entire mantle surface 17.

It is also advantageous if, the material of the front surface of the base differs from the material of at least one engaging projections mantle surface where they are attached. Such an arrangement can be achieved by the use of base film and preform projections comprised of different materials, with the use of compatibilizing layers if necessary, as discussed previously. It is even more advantageous if the material of the front surface of the base is softer than the material of the mantle surface of the at least one engaging projection as determined, for example, by differing Shore hardness values.

It is also advantageous for some uses if the fastener base is elastically extensible within a plane of the base, and the material of the mantle surface of the at least one engaging projection is non elastomeric. The base can comprise elastomer materials including elastic laminates or the like. This can make an elastic fastener product, which can be especially beneficial, for example, with diapers and wrapping tapes.

In addition, the invention fastener can also be used in other fields, such as in self adhesive fastener tapes for fixing carpets or polymer sheets to floors or tiles and fabrics to walls of a room.

The invention fastener can also be formed on the surface of a variety of base materials. This could be a film as described above but could be any suitable surface such as a fabric, nonwoven, metal sheet or foil, molded plastic, paper, breathable film, laminate etc, as described above for the first method. For example, engaging projections could be formed on a water insulating membrane used for insulating flat roofs of buildings against rain. This membrane could then be fixed on top of a nonwoven felt on the roof. This system would provide water insulation in combination with a beneficial, lateral vapour migration in the felt, under the insulating membrane.

As it has been said, it is a further object of the present invention to provide improved disposable diapers using the invention fastener.

In this aspect, a disposable diaper comprises:

a bodyside surface;

an opposite, outer surface, comprising a nonwoven fabric;

at least one male fastening component of the present invention for fixing the diaper about a wearer;

at least one female fastening component, comprising fabric, for separably engaging with the at least one male fastening component during the fixing. The female fastening component may be formed by the nonwoven fabric on the outer surface of the diaper. The separable engagement between the at least a portion of the nonwoven fabric of the outer surface of the diaper and the at least one male fastening component of the invention preferably has a shear strength of at least 4.9N.

The term "diaper", as used herein, also includes infant training pants, incontinence garments and the like. The said portion of the nonwoven fabric of the outer surface can be a strengthened portion where, the fibers of the nonwoven of the outer surface take part in engaging with the male fastening component. The said portion can be strengthened, for example, by providing a sufficiently stiff film layer under the nonwoven or by impregnating the nonwoven of the outer surface etc. The term "shear strength" refers to a peak shear strength or force achieved during a shear separation of the male fastener from the female fastener component. An appropriate selection of the nonwoven on the outer surface of the diaper and the male fastener component of the present invention will result in the fastener being capable of engaging with the nonwoven outer shell of the diaper strongly enough to securely keep the soiled diaper in a folded state without a separately provided loop. With a suitable selection of a nonwoven on the outer surface of the diaper, the fastener can be attachable to any suitable point of the diaper outer shell and the attachment of fixing is comfortable and secure. Preferably, the whole of the nonwoven of the outer surface is such a suitable nonwoven.

To make it even more secure, it is preferable if, in the diaper, the separable engagement, between the engagable portion of the nonwoven fabric of the outer surface and the at least one male fastening component of the invention, has a shear strength of at least 9.8 N.

In an even more preferable diaper, the at least one female fastening component is constituted by at least a portion of the nonwoven fabric of the outer surface.

Such a selection of the nonwoven of the outer surface of the diaper, and the suitable kind of fastener makes using of a separate frontal tape comprising a special loop fabric in the landing zone unnecessary. This provides considerable cost saving. It just needs a suitable surface area selected for the fastener to achieve a desired fixing strength for securing the diaper around a wearer during use.

It is even more preferable, if in the latter diaper, the separable engagement between at least a portion of the nonwoven fabric of the outer surface of the diaper and the at least one invention male fastening component has a shear strength of at least 2.5 N/cm². Here the necessary shear strength is specified as a shear strength specific of 1 cm² unit area of contact surface between the nonwoven and the fastener.

To make it even more secure, it is further preferable if, in the diaper, the separable engagement, between at least a portion of the nonwoven fabric of the outer surface and the at least one male fastening component, has a shear strength of at least 3.5 N/cm².

It is a further object of the present invention to provide an improved wrapping tape. Such wrapping tape has a first side with an exposed textile or nonwoven material, and an opposite second side, comprising a male fastening component of the present invention suitable for engaging with the textile or nonwoven material for fixing the wrapping tape around an object. The textile or nonwoven material also includes low loft fabrics with some free fibers capable of mechanically engaging with the male fastener materials of the present invention. The advantages of this wrapping tape are that it has fine touch, is easy to write upon with ink, can be flexible, extensible or stretchable, is inexpensive, and is novel in its appearance. With a porous, e.g., micro-perforated or nonwoven, base and a suitable nonwoven loop textile, this wrapping tape even be used as house wrap.

DESCRIPTION OF THE PREFERRED EMBODIMENTS

Reference is made to the method depicted in FIG. 1a. Using a subset method of the invention, polymer powder granules are provided, as polymer particles 36. A base 4 sheet is fed into the system from a suitable source. A contact release surface 40 is provided on a release conveyor 39 that is driven around two drive rollers 11. The contact release surface 40 is kept horizontal.

Figure 1B:
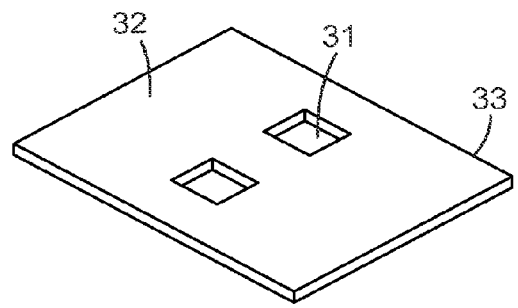
Figure 1C:
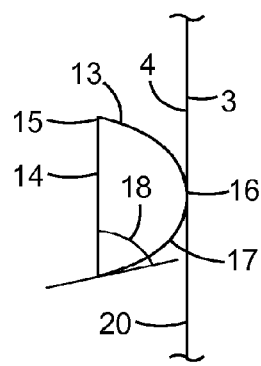

At the beginning of the operation cycle, the horizontal contact release surface 40 is kept at an elevated temperature by a hot plate 24. This could be done under the release conveyor 39, though further hot chambers, on the top side of a release conveyor, could also be utilized. A scatter unit 42 is used to evenly disperse the polymer particles 36 onto a stationary mask 31, (a perspective view of a possible stationary mask 31 is shown in FIG. 1b), with solid regions 33 intersecting falling particles and open areas 32 allowing particles to fall onto the moving release surface 40 in a predetermined pattern. The mask could also in this version be apertures built into the scatter unit 42. With a stationary mask the particles will be deposited in continuous rows in the continuous method shown in FIG. 1a. The rows can be made discontinuous by interrupting the flow of particles for a period of time. The rows can be made to oscillate if the stationary mask is moved in the crossweb direction in a oscillatory fashion. The particles are distributed on the contact release surface 40 to form preform projections 37. The release surface 40 can be cooled prior to the heating element 24. Cooling is also important for later preserving the contact angle of the preform projections 37, and can be provided by a steel cooling plate 45 at a controlled temperature under the contact release surface 40. The cooled preform projections 44 are made solid and suitable for contacting with the front surface 20 of the base 4. The base 4 is laid over the preform projections 44 on the contact release surface 40. The front surface 20 of the base 4 contacts the terminal ends of the preform projections 44. A hot air blowing unit 23 can be fixed above the back surface 3 of the base 4. Hot gas 21 is blown on the back surface 3 of the base 4, which could be done while the release conveyor 39 and the base 4 are together kept in motion in a lateral direction 25. Each point of the base 4 is exposed to the hot air for a time sufficient to soften and fix the terminal ends of the preform projections 44 to the front surface 20 of the base 4. Then the base 4 is cooled, which could be done by air blower 12. The base 4, with the engaging projections 13 fixed thereto, is separated and removed from the contact release surface 40, and is then wound up on a reel (not shown).

Using this method the engaging projections 13 formed will have flattened tops 14, with a rim overhanging the base 4 typically in all directions, and bordered, typically all around, by an edge 15 whose angle 18 essentially corresponds to the contact angle 38. The vast majority of the engaging projections 13 will strictly taper (strictly convex), in each side view thereof, from the flattened top 14 to the attached end 16 at the front surface 20 of the base 4 (This also applies to the engaging projections discussed hereafter).

Figure 2B:
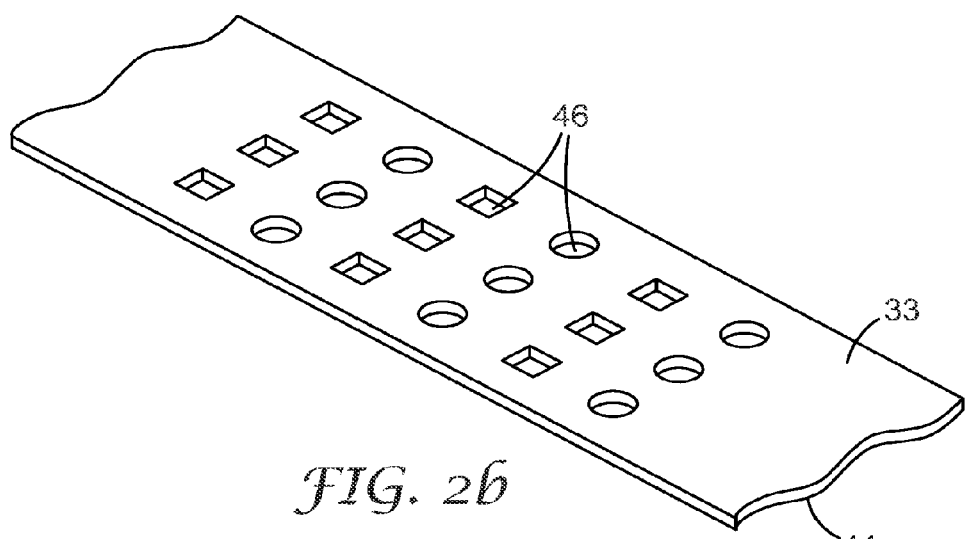
Figure 2A:
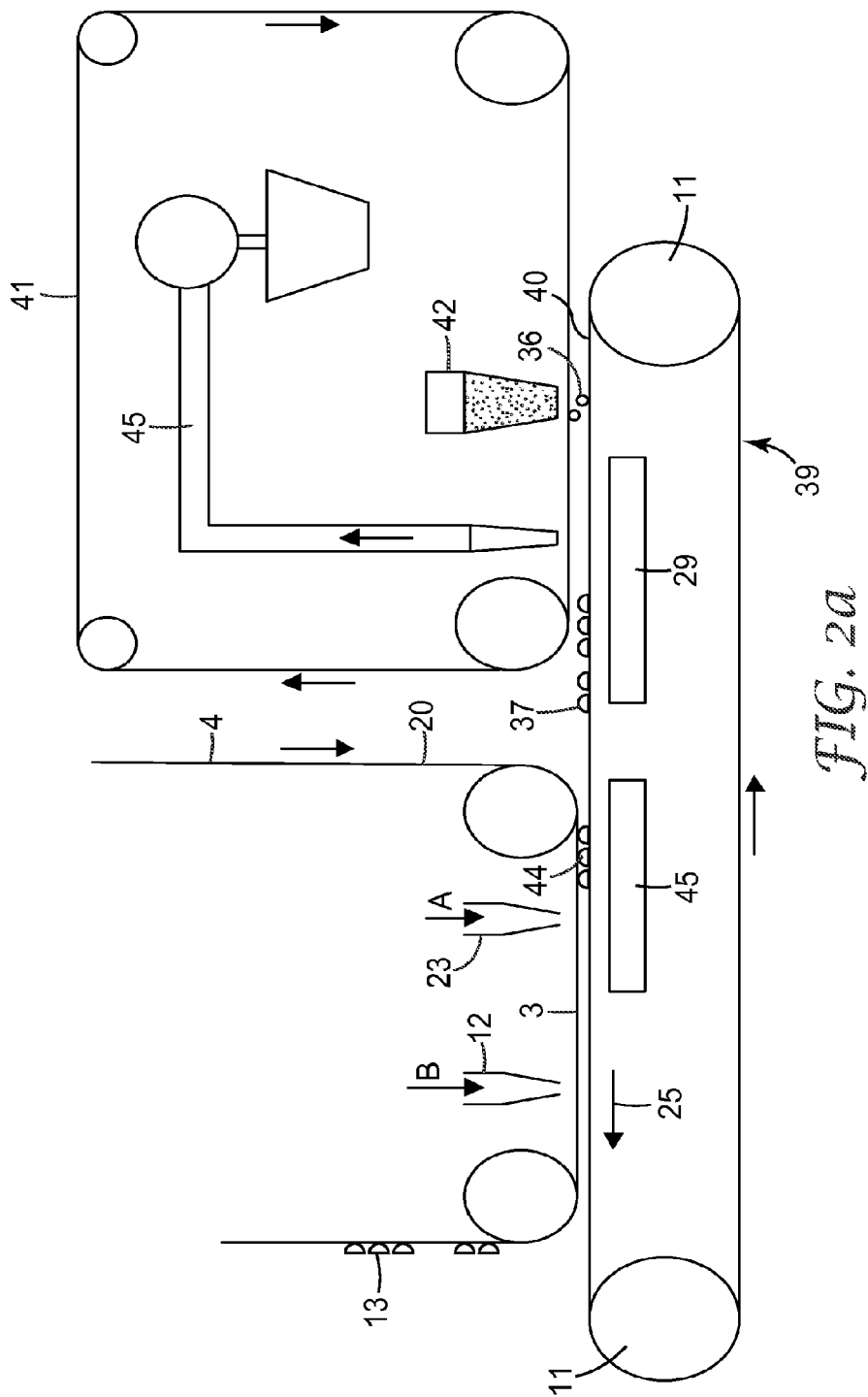
FIG. 2a is a schematic side view of a second apparatus for manufacturing a fastener of the invention.

Reference is made to the method depicted in FIG. 2a. Using a subset method of the invention polymer powder granules are provided, as polymer particles 36. A base 4 sheet is fed into the system from a suitable source. A contact release surface 40 is provided on a release conveyor 39 that is driven around two drive rollers 11. The contact release surface 40 is kept horizontal. A moving mask 41 is provided in the form of an endless belt.

At the beginning of the operation cycle, the horizontal contact release surface 40 is kept at an elevated temperature by a hot plate 29. This could be done under the release conveyor 39, though further hot chambers, on the top side of a release conveyor, could also be utilized. A scatter unit 42 is used to evenly disperse the polymer particles 36 onto the moving mask 41 (A perspective view of a possible moving mask 41 is shown in FIG. 2b. This mask would serve to deposit particles in a pattern of squares and circles). Solid regions 33 of the mask 31 intersect falling particles and open areas 46 of the mask 31 allow particles to fall onto the release surface 40 in a predetermined pattern determined by the mask when the moving mask 41 and the contact release surface 40 are moving at the same relative speeds. With a moving mask the particles can be deposited in discrete shapes in the continuous method shown in FIG. 2a. In this case the mask should be rotating at approximately the same speed as the release surface 40, at least such that the particles from one mask open area 46 do not end up getting randomly scattered on the release surface 40 or merged with particles from an adjacent open area 46. If it is desired to provide the shaped regions (e.g. squares, circles, etc.) with minimum distortion, the mask should move in tandem with the contact release surface; that is, at very close to the same speed. The regions with particles could be distributed in other patterns if the moving mask rows are made to oscillate or move in the in the cross direction. As in the method of FIG. 1, the particles are that are distributed on the contact release surface 40 form preform projections 37, then form cooled preform projections 44, then are contacted with and attached to the front surface 20 of base 4, as described for the embodiment of FIG. 1. Particles that intersect the solid areas 43 of mask 41 may be removed, for example by contacting the moving mask with a sticky roll, vacuum agitation or the like. Ideally the particles are removed for recycling to the scatter unit 42, for example by use of vacuum scavenging system 45.

Figure 3A:
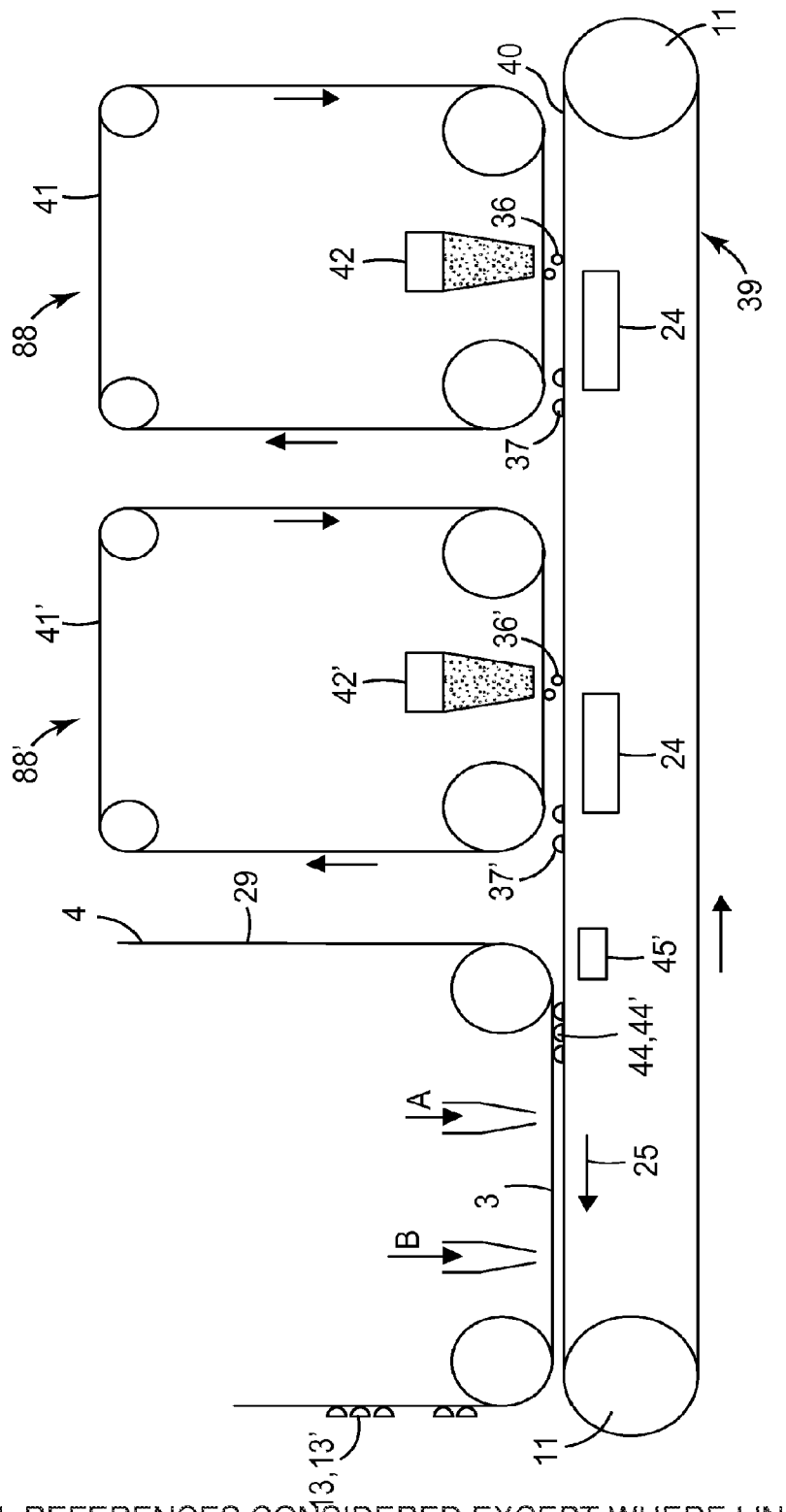
FIG. 3a is a schematic side view of a third apparatus for manufacturing a fastener of the invention.

A further subset method is depicted in FIG. 3a. A first type of polymer powder granules are provided, as polymer particles 36. A base 4 sheet is fed into the system from a suitable source. The contact release surface 40 is provided on a release conveyor 39 which is driven around two drive rollers 11. The contact release surface 40 is kept horizontal. A first moving mask 41 and a second moving mask 41' are provided in the form of endless belts.

Figure 3B:
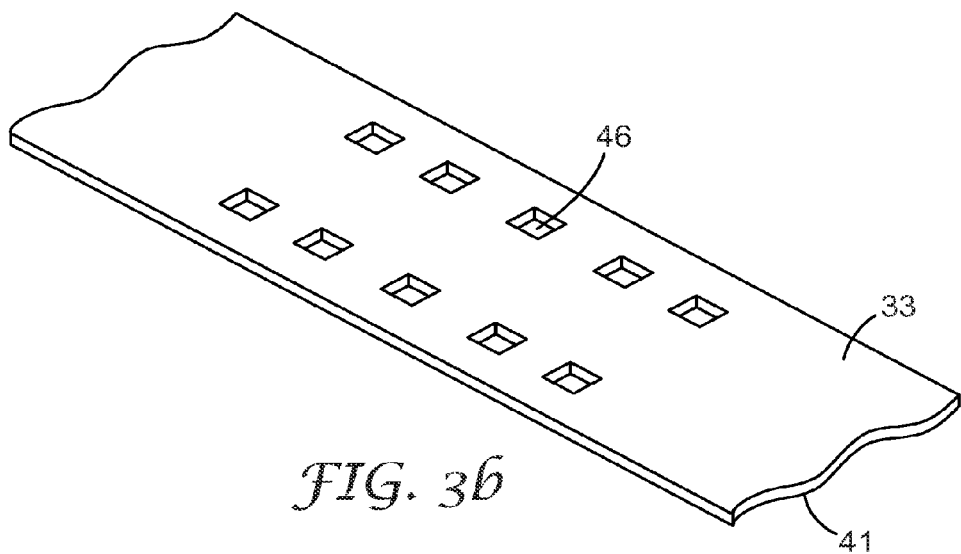
Figure 3C:
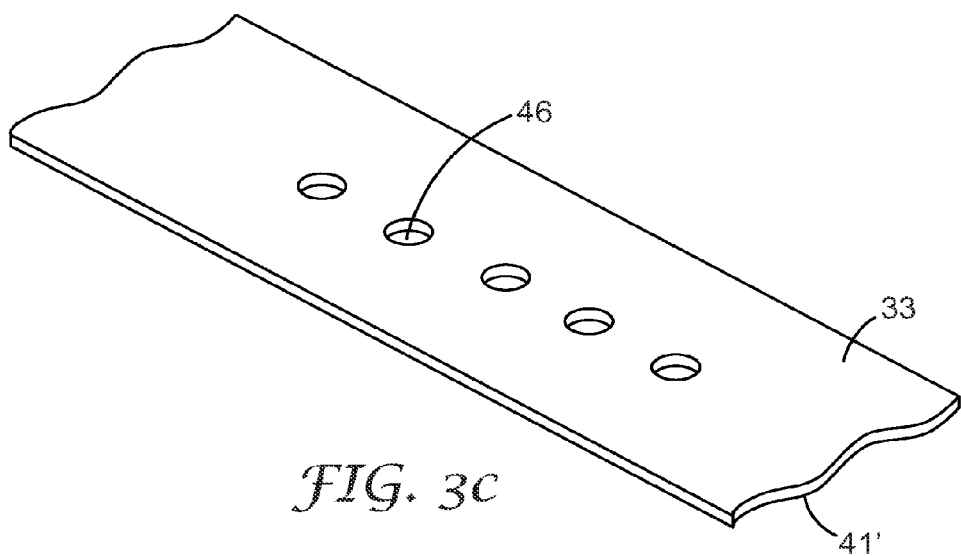

At the beginning of the operation cycle, the horizontal contact release surface 40 is kept at an elevated temperature by a hot plate 24. This could be done under the release conveyor 39, though further hot chambers, on the top side of a release conveyor, could also be utilized. In a first deposition station 88, a first scatter unit 42 is used to disperse the polymer particles 36 onto the first moving mask 41 (A perspective view of a first moving mask 41 is shown in FIG. 3b.). Solid regions 33 of the mask intersect falling particles and open areas 46 allow particles to fall onto the contact release surface 40 in a predetermined pattern. Movement of the mask 41 with the contact release surface can be synchronized as described in the method of FIG. 2a. The particles so deposited form the first type of preform projections 37 in discrete areas on the contact release surface. Optionally, the deposited preform projections 37 can be cooled as previously described. The contact release surface 40 is then passed through a second deposition station comprising a second moving mask 41' and a second scatter unit 42' which is used to disperse a second type of polymer powder granules 36' (A perspective view of a possible second moving mask 41' is shown in FIG. 3c). Solid regions 33 of the mask intersect falling particles and open areas 46 allow particles to fall onto the release surface 40 in second areas of the contact release surface in a predetermined pattern. Movement of the second mask is synchronized with the contact release surface as done with the first mask. The contact release surface may be heated (or reheated, if a cooling step was used subsequent to the first deposition) via second heating element 24 as done for the first deposition. The particles so deposited form the second type of preform projections 37'. The contact release surface bearing the preform projections is then passed by cooling element 45 so as to form cooled preform projections 44 and 44', after which base 4 is contacted with the terminal ends of the cooled preform projections attaching them to the base and forming engaging elements 13 and 13', in the manner described for the embodiment of FIG. 1a. Vacuum scavenging systems (not shown) as described in FIG. 2a may be used to retrieve the polymer particles that intersected the solid areas 33 of mask 41. This embodiment would serve to provide a base film bearing rows of discrete circles of engaging projections of one type, and discrete squares of engaging projections of another type.

Figure 4B:
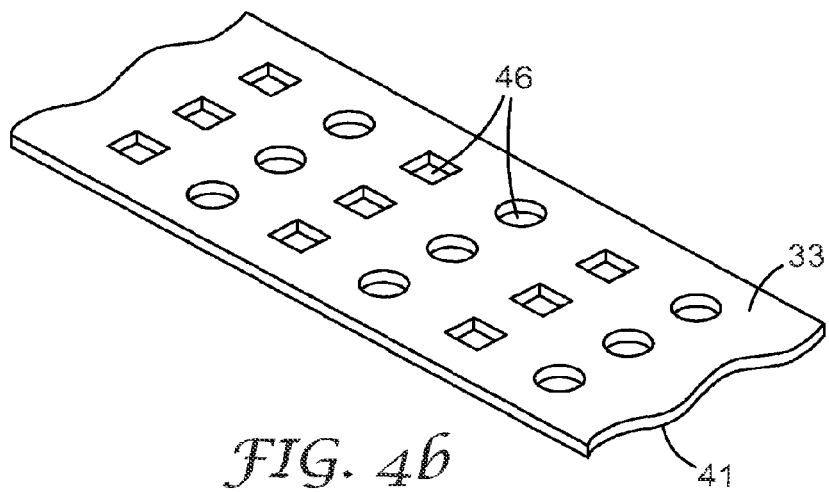

The method depicted in FIG. 4a is a further first subset method of the invention. Using this method of the invention polymer powder granules are provided, as polymer particles 36'. A base 4 sheet is fed into the system from a suitable source. The contact release surface 40 is provided on a release conveyor 39 that is driven around two drive rollers 11. The contact release surface 40 is kept horizontal. An electrostatic deposition unit 52 is provided, comprising two electrodes. Electrode 54 is held at low voltage (typically, zero or ground voltage) while electrode 53 is held at a higher voltage. Electrode 53 is positioned underneath a moving mask 41 while electrode 54 is positioned above a contact release surface 40. Moving mask 41 is provided with solid regions 43 and with open areas 46, and can be synchronized with the speed of contact release surface 40 as described above.

At the beginning of the operation, particles 36 are dispensed into a vertically configured electrostatic deposition unit 52 (not shown) such as by being injected laterally into the gap between lower plate 53 and moving mask 41. This may be done by means of e.g. spraying the particles or bringing them into the gap via a belt conveyor from which the particles are dislodged by the electric field. Or, the electrode 53 could be a rotating drum electrode, a belt electrode or the like for both conveying and charging the particles. Under the influence of the electric field established by electrodes 53 and 54, particles 36 develop a charge to comprise charged particles 36', and are then driven vertically upwards. The charged particles 36' that penetrate through the open areas of moving mask 41 continue to move upwards until they impinge on contact release surface 40. The charged particles may be held on the contact release surface 40 against the force of gravity by the residual electrostatic force between the particles and the contact release surface until the contact release surface moves such that the particles are atop the release conveyor and no such assistance is necessary. The release conveyor then continues such that the particles are carried into proximity with heating element 24 (as in the configuration illustrated in FIG. 4a). Alternatively, heating element 24 can be placed such that the particles 36' are heated immediately upon deposition (as in the embodiment described with reference to FIG. 1), so that wetting forces may assist in holding the particles on the release surface, until the release conveyor 39 moves sufficiently such that the particles 36' are on the upward facing surface of the release conveyor 39. Subsequent processing to contact and attach the preform projections 36 to the base film are as described previously. Particles that intersect solid areas 43 of mask 41 may fall off on their own due to gravity (once the moving mask carries them out of the electric field), or can be removed such as with a vacuum scavenging system as described for FIG. 2a.

Figure 5B:
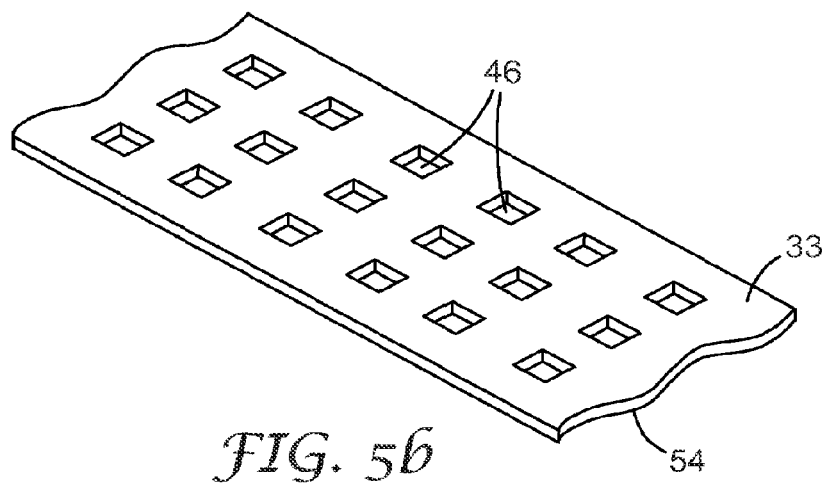
Figure 5A:
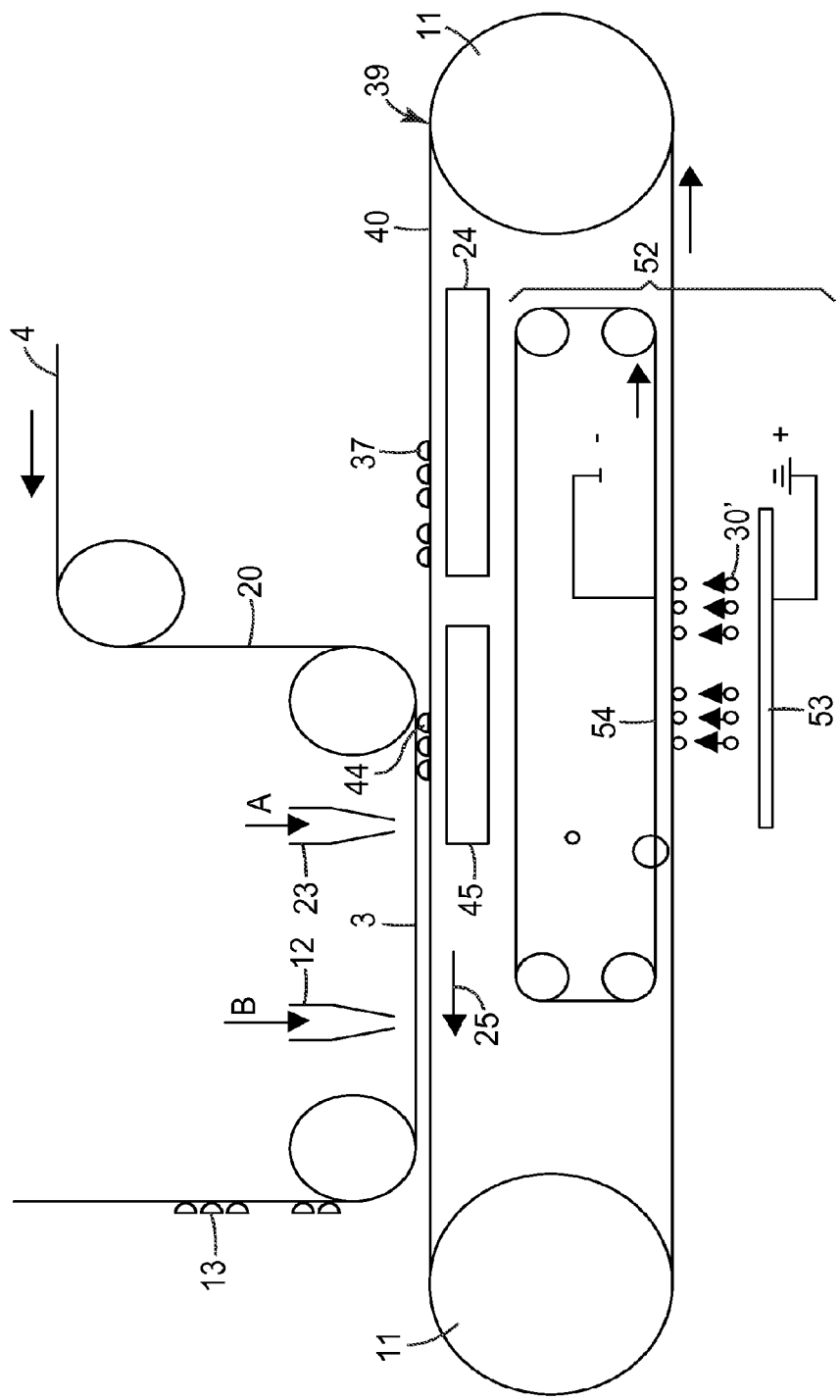
FIG. 5a is a schematic side view of a fifth apparatus for manufacturing a fastener of the invention.

The method depicted in FIG. 5a is a further subset method of the invention This method is similar to that of FIG. 4a except that no mask is used; rather, electrode 54 is provided as a rotating patterned belt electrode, e.g. a metal belt electrically connected to counterpart electrode 53. Moving belt electrode 54 is positioned behind (above) the moving contact release surface 40 and is typically synchronized to move at the a matching speed as discussed above. In one embodiment, electrode 54 comprises a metal belt that has regions 46 cut out, as shown in the perspective view of FIG. 5b. Using a method of the invention, polymer powder granules are injected into the gap between lower electrode 54 and contact release surface 40 and develop a charge. The charged polymer particles 36' will then be driven upwards, concentrating preferentially along lines that are aligned with solid sections 33 of belt electrode 54 (i.e. being less concentrated along lines that align with the cutout holes in electrode 54). The particles thus impinge on release surface 40 in a pattern corresponding to that established by the patterned belt electrode 54. In an alternative embodiment, electrode 53 can also be a patterned moving belt electrode, and can move in tandem with electrode 54, so as to achieve further concentration of the particles in the desired areas of the contact release surface. Further processing of the particles on base sheet 4 is as described with regard to FIG. 4a (In this instance there is no mask from which particles need be removed.)

Figure 6A:
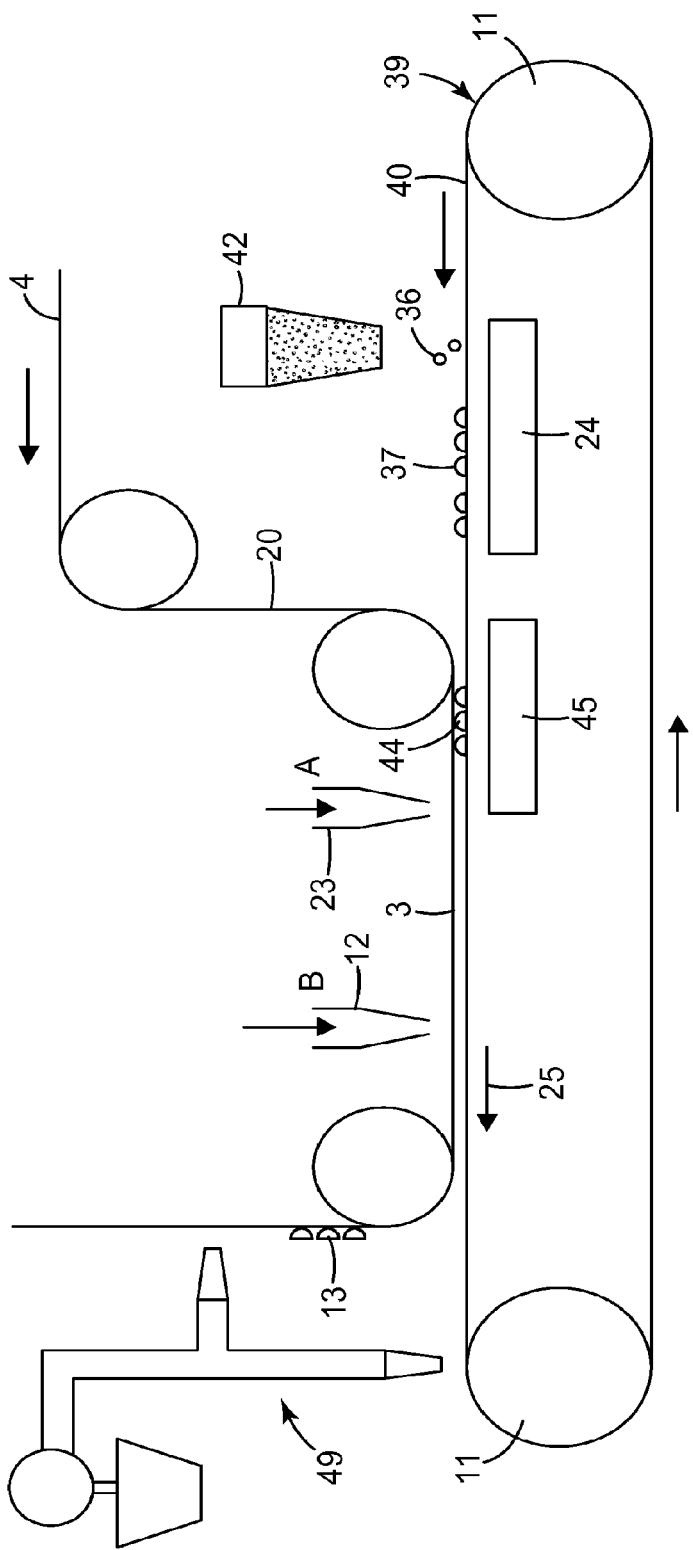
FIG. 6a is a schematic side view of a sixth apparatus for manufacturing a fastener of the invention.
Figure 6G:
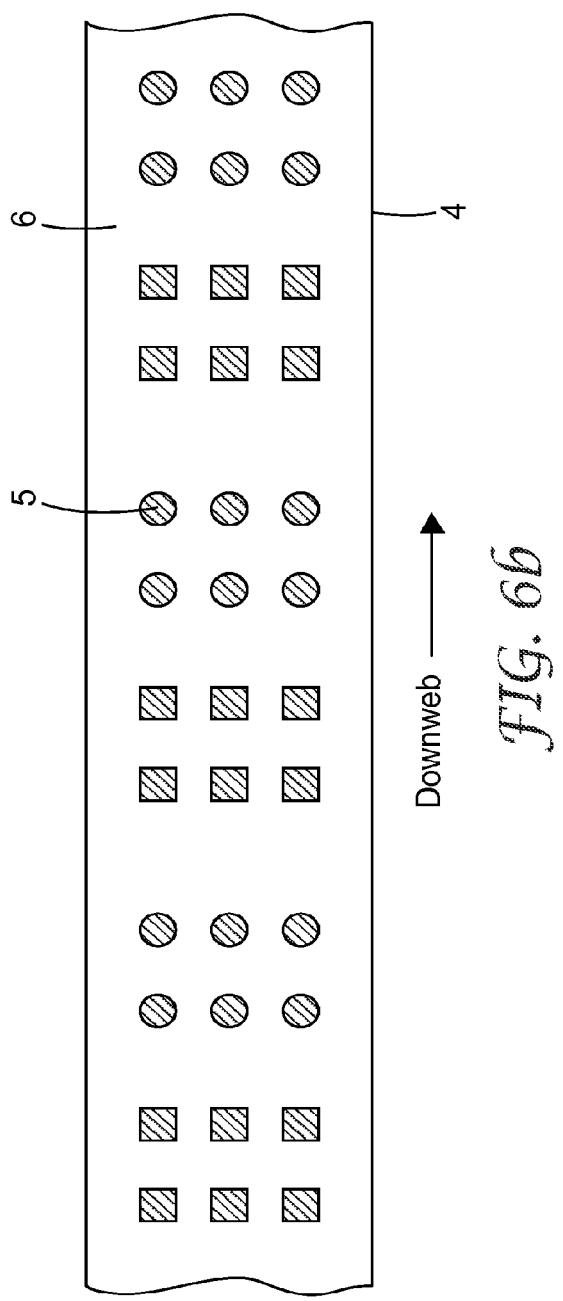

The method depicted in FIG. 6a is a subset method of the invention. Using this method of the invention, polymer powder granules are provided, as polymer particles 36. A base 4 sheet is fed into the system from a suitable source. The base 4 sheet in this embodiment is provided with regions 5 (FIG. 6b) that will preferably bond to the preform projections and areas 6 that will preferably not bond to the preform projections (as shown in FIG. 6b). The contact release surface 40 is provided on a release conveyor 39 that is driven around two drive rollers 11. The contact release surface 40 is kept horizontal. No mask is used.

At the beginning of the operation cycle, the horizontal contact release surface 40 is kept at an elevated temperature by a hot plate 24. This could be done under the release conveyor 39, though further hot chambers, on the top side of a release conveyor, could also be utilized. A scatter unit 42 is used to evenly disperse the polymer particles 36 onto the release surface 40. The particles are distributed on the contact release surface 40 to form preform projections 37. Cooling is provided by a cooling plate 45 at a controlled temperature under the contact release surface 40 forming cooled preform projections 44. The cooled preform projections 44 are made solid at least in part. The base 4 is laid over the preform projections 44 on the contact release surface 40. The front surface 20 of the base 4 contacts the terminal ends of the preform projections 44. A hot air blowing unit 23 can be fixed above the back surface 3 of the base 4. Hot gas 21 is blown on the back surface 3 of the base 4, which could be done while the release conveyor 39 and the base 4 are together kept in motion in a lateral direction 25. Each point of the base 4 is exposed to the hot air for a time sufficient to soften and fix the terminal ends of the preform projections 44 to the front surface 20 of the base 4. The base is then cooled which could be done by air blower 12. The base 4, together with the engaging projections 13 fixed thereto, in the regions 5 that will preferably bond to the preform projections 44, is separated and removed from the contact release surface 40. Unbonded preform projections 44 on nonbonding areas 6 of the base film 4, or on the contact release surface 40, may be removed such as by vacuum removal device 49 or by sticky rolls.

Figure 7A:
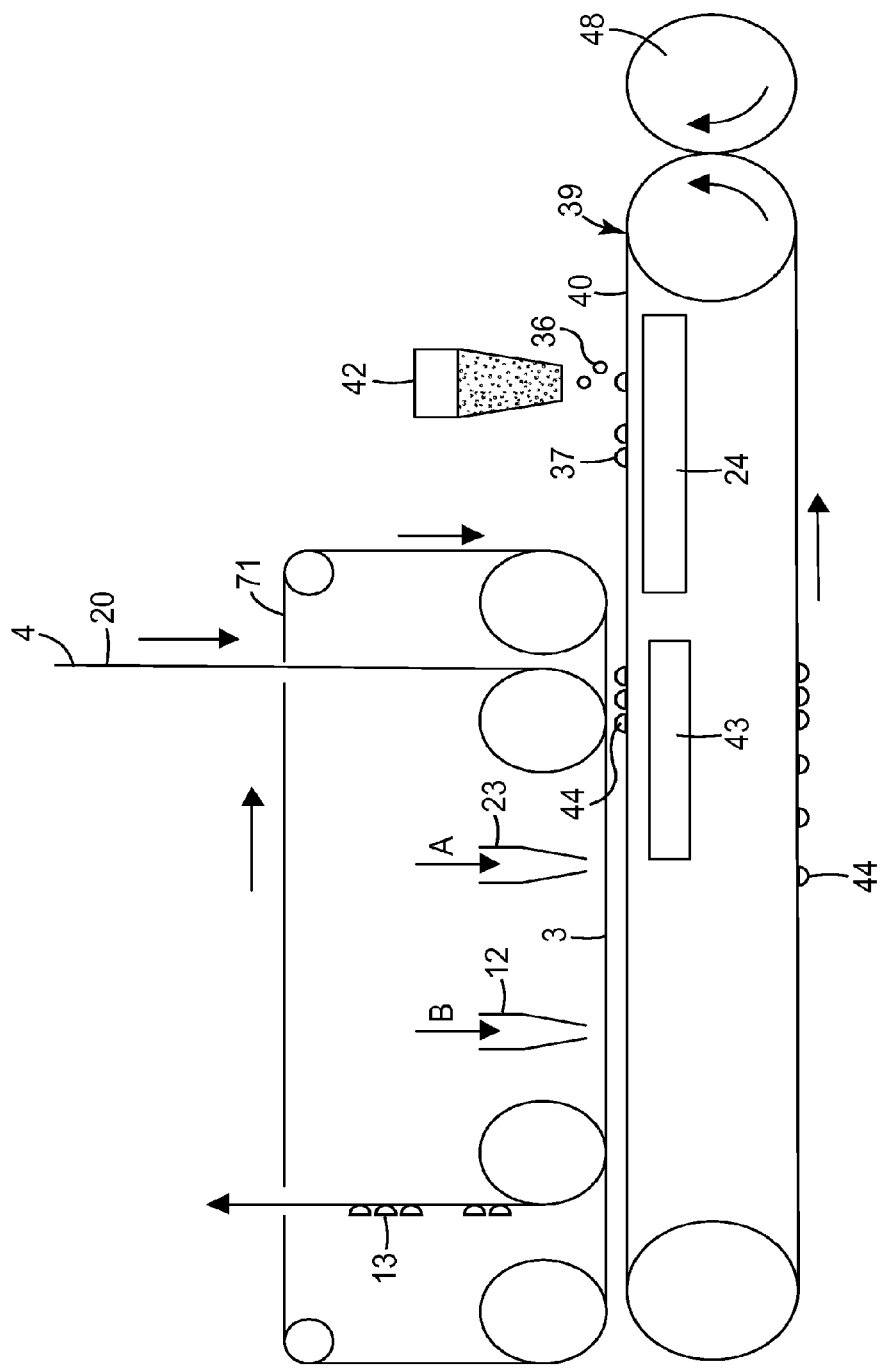
FIG. 7a is a schematic side view of a seventh apparatus for manufacturing a fastener of the invention.
Figure 7B:
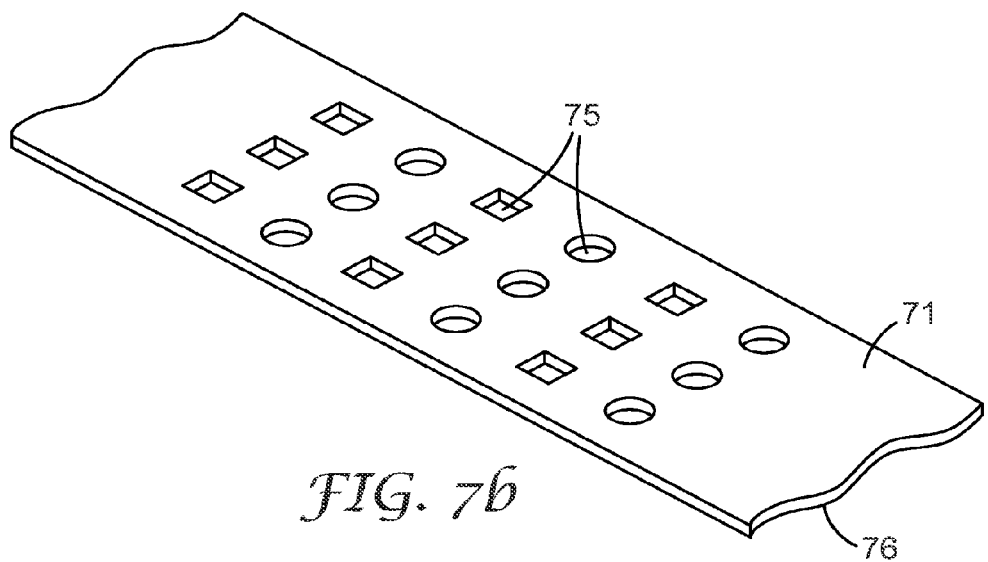

The method depicted in FIG. 7a is a further subset method of the invention. Using this method of the invention, polymer powder granules are provided, as polymer particles 36. A base 4 sheet is fed into the system from a suitable source. The base 4 sheet in this embodiment is masked using a transfer masking belt 71 provided with open areas 75 that will allow the preform projections to contact the base sheet 4 and solid areas 76 that will not allow preform projections to contact base sheet 4 (In this configuration the masking belt 71 should be sufficiently thin that the preform projections are able to protrude or pushed through the open areas so as to contact the base sheet.). One such belt is shown in FIG. 7b. The contact release surface 40 is provided on a release conveyor 39 that is driven around two drive rollers 11. The contact release surface 40 is kept horizontal.

At the beginning of the operation cycle, the horizontal contact release surface 40 is kept at an elevated temperature by a hot plate 24. This could be done under the release conveyor 39, though further hot chambers, on the top side of a release conveyor, could also be utilized. A scatter unit 42 is used to evenly disperse the polymer particles 36 onto the release surface 40. The particles are distributed on the contact release surface 40 to form preform projections 37. Cooling is provided by a cooling plate 45 at a controlled temperature under the contact release surface 40 so as to form cooled preform projections 44. The cooled preform projections 44 are made solid and suitable for contacting with the front surface 20 of the base 4. The base 4 is laid over the preform projections 44 on the contact release surface 40. The front surface 20 of the base 4 contacts the terminal ends of the preform projections 44 through the open areas 75 provided in the transfer masking belt 71. A hot air blowing unit 23 can be fixed above the back surface 3 of the base 4. Hot gas 21 is blown on the back surface 3 of the base 4, which could be done while the release conveyor 39 and the base 4 are together kept in motion in a lateral direction 25. Each point of the base 4 is exposed to the hot air for a time sufficient to soften and fix the terminal ends of the preform projections 44 to the front surface 20 of the base 4. Then the base is cooled which could be done by air blower 12. The base 4, together with the engaging projections 13 fixed thereto in the areas opens through the open areas 75 is separated and removed from the contact release surface 40, which could then wound up in a reel. Any remaining preform projections 44 on the contact release surface or on the transfer masking belt 71 may be removed by a removal device such as described for FIG. 6a.

EXAMPLE

Method for Discrete Deposition of Particles on a Base Film

A process was set up similar to that depicted in FIG. 2a. A contact release surface was provided comprising a polytetrafluoroethylene-coated glass fiber web, with a slightly textured surface, available from Lörincz kft, Hungary, under the designation Chemglas 100-6. The surface energy of the contact release surface 40 was about 18.5 mJ/m$^2$. The contact release surface was present as a horizontal sheet on the top surface of a shuttle that could be moved laterally, in order to simulate the continuous belt conveyor system of FIG. 2a.

Polypropylene particles of size range of about 200-500 microns diameter were placed into a gravity-operated scatter unit (a hopper with a feeding wheel and an underlying screen).

At the beginning of the operation cycle, the horizontal contact release surface was brought to a temperature of about 170° C. by a heating element located underneath the conveyor shuttle. A masking template with discrete shape patterns similar to that shown in FIG. 2b was placed on the top of the contact release surface 40. The shuttle was moved laterally at approximately 0.17 meters per second underneath the scatter unit, which was used to disperse the polymer particles on the heated contact release surface at an average density of about 16 g/m² in the particle deposited regions. The particles were heated by the heat of the contact release surface and thereby softened or melted into a semiliquid state. Several seconds after the particles were distributed on the release surface, they formed preform projections. Then the release surface was moved over a cooling plate and halted in position so as to cool the contact release surface to a temperature of about 70° C. The preform projections were thus made solid and suitable for contacting with the front surface of a base film.

A base film was provided comprising a polypropylene film with a basis weight of 74 g/m² (available under product designation FL-3054 from 3M Company, St Paul, Minn.). The base film was laid over the preform projections on the contact release surface such that the front surface of the base contacted the terminal ends of the preform projections. A hot air blowing unit which was fixed about 15 mm above the back surface of the base film, was used to blow air at a measured temperature of about 600° C. against the back surface of the base. The shuttle, which carried the release contact surface with the preform projections and base film, was moved laterally at approximately 0.17 meters per second underneath the hot air blowing unit. Each point of the base was thus exposed to the hot air, for a short period (typically one second or less), such that the base was softened enough to be fixed with the terminal ends of the preform projections. The terminal ends also melted from the heat to a suitable extent to fuse the preform projections to the base. The base film with attached projections was then cooled. The base, together with the engaging projections fixed thereto, was then removed from the contact release surface.

What is claimed is:

1. A hook fastener capable of engaging a suitable loop fabric, the hook fastener comprising:
   a base comprising a front surface and a back surface; and
   a multiplicity of engaging projections extending from the front surface of the base, at least one of said engaging projections comprising:
      a substantially flat top surface having a top surface edge;
      an attached end fixed to the front surface of the base; and
      a mantel surface extending from the top surface edge to the attached end, at least one contour line of a side view of the mantel surface being strictly convex from the top surface edge to the attached end;
   wherein a plurality of said engaging projections are arranged in a region on the base to form one or more shapes on the base.

2. The hook fastener of claim 1 wherein the plurality of engaging projections forming one of said shapes forms a discrete shape.

3. The hook fastener of claim 1 wherein the plurality of engaging projections form one or more shapes which extends substantially continuously in one dimension of the base.

4. The hook fastener of claim 1 wherein one or more shapes formed by the plurality of engaging projections is formed by a region having a relatively high density of engaging projections.

5. The hook fastener of claim 1 wherein one or more shapes have a minimum width dimension less than the width of the base.

6. The hook fastener of claim 1 wherein one or more shapes have a minimum width dimension of greater than 1 mm.

7. The hook fastener of claim 1 wherein one or more shapes have a minimum width dimension of greater than 4 mm.

8. The hook fastener of claim 1 wherein one or more shapes are surrounded by secondary areas having a different density of engaging projections.

9. The hook fastener of claim 8 wherein the secondary areas have little or no engaging projections.

10. The hook fastener of claim 8 wherein the one or more shapes have an average density of engaging projections of at least 1 gsm, and the secondary regions have an average density of engaging projections of less than 0.5 gsm.

11. The hook fastener of claim 8 wherein the one or more shapes have an average density of engaging projection of at least 2 gsm, and the secondary regions have an average density of engaging projections of less than 0.5 gsm.

12. The hook fastener of claim 1 wherein one or more shapes form ornamental images.

13. The hook fastener of claim 12 wherein the base has a preprinted image on at least one of the front surface or the back surface.

14. The hook fastener of claim 1 wherein there are a plurality of repeating discrete shapes.

15. The hook fastener of claim 1 wherein there are two or more regions forming shapes which are formed of different types of engaging projections.

16. The hook fastener of claim 1 wherein the one or more shapes are surrounded by secondary regions having different types of engaging projections.

17. The hook fastener of claim 1 wherein the base is provided with a pressure sensitive adhesive layer at least in areas adjacent the regions forming the one or more shapes.

18. The hook fastener of claim 1 wherein the entire mantel surface is strictly convex.

19. The hook fastener of claim 1 wherein the attached end has a diameter and the top surface edge has a diameter wherein the attached end diameter is smaller than the top surface edge diameter.

20. The hook fastener of claim 1 wherein at least some of the engaging projections further comprise an edge angle defined by the top surface and the mantel surface, wherein the edge angle is from 10 to 85 degrees.

21. The hook fastener of claim 20 wherein the edge angle is from 30 to 80 degrees.

22. The hook fastener of claim 1 wherein the at least some of the engaging projections are randomly distributed in the one or more shapes on the front surface of the base.

* * * * *

UNITED STATES PATENT AND TRADEMARK OFFICE
CERTIFICATE OF CORRECTION

| | | |
|---|---|---|
| PATENT NO. | : 7,636,988 B2 | Page 1 of 1 |
| APPLICATION NO. | : 11/530499 | |
| DATED | : December 29, 2009 | |
| INVENTOR(S) | : Zhiqun Zhang | |

It is certified that error appears in the above-identified patent and that said Letters Patent is hereby corrected as shown below:

Column 10

Line 67; Delete "force" and insert -- forces --, therefor.

Column 15

Line 32; Delete "mj/m$^2$." and insert -- mJ/m$^2$. --, therefor.

Column 22

Line 31; After "fastener" delete "at least one".

Column 28

Line 49; Delete "opens" and insert -- open, --, therefor.

Column 30

Line 2; Claim 3, delete "extends" and insert -- extend --, therefor.

Line 48; Claim 19, after "diameter" insert -- , --.

Signed and Sealed this
Eleventh Day of January, 2011

David J. Kappos
*Director of the United States Patent and Trademark Office*